(12) United States Patent
Hukari et al.

(10) Patent No.: US 9,028,777 B2
(45) Date of Patent: May 12, 2015

(54) AUTOMATED CELLULAR MATERIAL PREPARATION

(75) Inventors: Kyle W. Hukari, Dublin, CA (US); Jason A. A. West, Pleasanton, CA (US); Michael A. Shultz, Bend, OR (US); Richard Milson, Citrus Heights, CA (US); Nikolas M. Isely, Moraga, CA (US); Michael C. DeRenzi, San Ramon, CA (US)

(73) Assignee: Fluidigm Corporation, South San Francisco, CA (US)

( * ) Notice: Subject to any disclaimer, the term of this patent is extended or adjusted under 35 U.S.C. 154(b) by 585 days.

(21) Appl. No.: 13/069,820

(22) Filed: Mar. 23, 2011

(65) Prior Publication Data

US 2011/0294205 A1 Dec. 1, 2011

Related U.S. Application Data

(60) Provisional application No. 61/316,555, filed on Mar. 23, 2010.

(51) Int. Cl.
| | | |
|---|---|---|
| *B01D 21/00* | (2006.01) | |
| *G01N 1/40* | (2006.01) | |
| *C12N 15/10* | (2006.01) | |
| *C12Q 1/68* | (2006.01) | |
| *G01N 35/10* | (2006.01) | |

(52) U.S. Cl.
CPC ............ *G01N 1/405* (2013.01); *C12N 15/1003* (2013.01); *C12Q 1/6806* (2013.01); *G01N 35/1095* (2013.01); *G01N 2035/1053* (2013.01)

(58) Field of Classification Search
USPC .................. 422/68.1, 82.01, 527; 436/180
See application file for complete search history.

(56) References Cited

U.S. PATENT DOCUMENTS

| | | | |
|---|---|---|---|
| 7,507,374 | B2 | 3/2009 | Gould et al. |
| 2003/0062310 | A1 | 4/2003 | Zare et al. |
| 2007/0015179 | A1 | 1/2007 | Klapperich et al. |
| 2007/0140904 | A1* | 6/2007 | Bremer et al. ............... 422/68.1 |
| 2008/0006535 | A1 | 1/2008 | Paik et al. |
| 2008/0200343 | A1* | 8/2008 | Clemens et al. ................. 506/9 |
| 2008/0264842 | A1 | 10/2008 | Hukari et al. |

OTHER PUBLICATIONS

Huh, et al., Development of a Fully Integrated Microfludic System for Sensing Infectious Viral Disease, Electrophoresis, 2008, 29:2960-2969.

Hukari et al., "A Completely Automated Sample Preparation Instrument and Consumable Device for Isolation and Purification of Nucleic Acids," Sep. 15, 2010, Journal of the Association for Laboratory Automation.

* cited by examiner

*Primary Examiner* — Jyoti Nagpaul
(74) *Attorney, Agent, or Firm* — Baker & Hostetler LLP

(57) ABSTRACT

Provided are cartridges and systems for effecting automated extraction, isolation, and purification of cellular components—such as nucleic acids—from a cellular sample in assay-ready form. Also provided are related methods of effecting such sample processing.

22 Claims, 36 Drawing Sheets

Figure 4

| ITEM NO. | PART NUMBER | DESCRIPTION | -01/QTY. |
|---|---|---|---|
| 1 | 100-00122-01 | CAP, CONSUMABLE | 1 |
| 2 | 100-00155-01 | MAIN BODY, CONSUMABLE | 1 |
| 3 | 100-00185-XX | ELUTION TIP, PPM INSERT, CONSUMABLE | 1 |
| 4 | 100-00187-XX | RING, COMPRESSION, CONSUMABLE, XSYL | 1 |
| 5 | 100-00212-XX | SLIDE, CONSUMABLE | 1 |
| 6 | 300-00134-04 | O-RING, QUAD, 0.070"ID x 0.210"OD | 1 |
| 7 | 300-00134-12 | O-RING, QUAD, 3/8"ID x 1/2"OD | 1 |
| 8 | 300-00136-01 | MAGNET, DISC, STIRRING, CONSUMABLE | 1 |
| 9 | 300-00135-16 | O-RING, 5/8"ID x 3/4"OD | 1 |
| 10 | 300-00135-04 | O-RING, 5/64"ID x 13/64"OD | 2 |

Extruded Tube and Main Body Weld Interface (IRAM)

Figure 7

| ITEM NO. | P/N | DESCRIPTION | QTY. |
|---|---|---|---|
| 1 | 100-00157-01 | CONSUMABLE MODULE, THERMAL BASE | 1 |
| 2 | 100-00158-01 | CONSUMABLE MODULE, THERMAL ELEMENT | 1 |
| 3 | 100-00160-01 | CONSUMABLE MODULE, SLIDE | 1 |
| 4 | 100-00161-01 | CONSUMABLE MODULE, THERMAL COVER | 1 |
| 5 | 100-00163-01 | CONSUMABLE MODULE, DRAWER | 1 |
| 6 | 100-00180-01 | CONSUMABLE MODULE, SENSOR FLAG | 1 |
| 7 | 100-00182-01 | CONSUMABLE MODULE, MAGNET HOLDER | 1 |
| 8 | 100-00188-01 | CONSUMABLE MODULE, BASE, SOLID | 1 |
| 9 | 100-00197-01 | BRACKET, MOUNTING, MOTOR, CONSUMABLE MODULE | 1 |
| 10 | 100-00198-01 | BRACKET, MOUNTING, CCA, CONSUMABLE MODULE | 1 |
| 11 | 100-00199-01 | BRACKET, MOUNTING, FAN, CONSUMABLE MODULE | 1 |
| 12 | 100-00224-01 | Colostomy Tube | 1 |
| 13 | 100-00232-01 | BRACKET, MOUNTING, MIXING MOTOR, CONSUMABLE | 1 |
| 14 | 100-00249-01 | NUT, LEAD SCREW, CONSUMABLE MODULE | 1 |
| 15 | 100-00250-01 | LEAD SCREW, SLIDE, CONSUMABLE | 1 |
| 16 | 250-00112-01 | CCA, CONTROLLER, CONSUMABLE MODULE | 1 |
| 17 | 300-00115-01 | Optek Slotted Optical Switch | 1 |
| 18 | 300-00120-01 | Standoff, 1.50X0.25, SS, #4-40 | 4 |
| 19 | 300-00123-01 | FAN, 25mmX10mm, 3.5CFM | 1 |
| 20 | 300-00124-01 | Washer, #6X0.438, STEEL | 8 |
| 21 | 300-00152-01 | 1/4" Tube ID X 1/8" NPT Fitting | 1 |
| 22 | 300-00153-01 | Ball-Nose Spring Plunger | 2 |
| 23 | 300-00161-01 | COMPRESSION SPRING, 0.812X0.312 | 4 |
| 24 | 300-00164-01 | MOTOR, DC, CORELESS WITH GEARBOX | 1 |
| 25 | 310-00100-06 | #2-56X0.625, SHCS, SS | 7 |
| 26 | 310-00102-02 | #4-40X0.250, SHCS, SS | 6 |
| 27 | 310-00106-01 | #2-56X0.0625, SET SCREW, SS | 4 |
| 28 | 311-00102-01 | M2, SHCS, SS | 2 |
| 29 | 300-00194-01 | DC MOTOR, 16mm OD, GEARED, 10021 | 1 |
| 30 | 310-00111-02 | #4-40X0.250, BHS, SS | 23 |

Figure 11

Feasibility of chemistries/process

- Standard chemistries
  - Chaotropic salts / silica membrane

- Spin column format
  - Disadvantages:
    - Can be highly variable
    - Requires a well trained technician
    - Processing time (> 1 hour for 12 samples).
    - Large starting sample volumes require multiple column loads.

Arcxis

AUTOMATED CELLULAR MATERIAL PREPARATION

RELATED APPLICATIONS

The present application claims the benefit of U.S. Provisional Application 61/316,555, "Automated Cellular Material Preparation," filed on Mar. 23, 2010, which application is incorporated herein in its entirety for all purposes.

TECHNICAL FIELD

The present invention relates to the field of biological analysis devices and the field of nucleic acid extraction from cell-containing samples.

BACKGROUND

Effective molecular diagnostic analysis and life science studies depend on effectively prepared samples—such as nucleic acids—for analysis. The majority of techniques utilized for sample preparation, however, entail laborious and time consuming processes to ensure reproducible and high-purity samples. Additionally, these techniques require technician hands-on time which is expensive and increases the chance of human error during the preparation.

Sample preparation represents the bottleneck to the majority of molecular diagnostic applications today in the life sciences fields and is cited as the most important factor in high quality gene expression studies. While the majority of development in the field of molecular diagnostics is devoted to improved methods for the detection and identification of disease related target analytes, less focus is devoted to the preparation of samples for these systems.

Sample preparation also represents a complex set of activities in the laboratory, including sample collection, lysis, separation of the biological macromolecules from a complex contaminant rich environment, purification of these separated macromolecules from remaining contaminants, and elution of the sample in solutions that are compatible with downstream analysis processes. While several automated sample preparation platforms exist, the majority of these systems require multiple bench top steps in addition to the automated functions of the process. With the increasing emphasis on high-throughput molecular diagnostics testing in the clinical environment, fast, reproducible methods and systems for sample preparation are required. Accordingly, there is a need in the art for devices and methods that perform rapid, reproducible sample preparations.

SUMMARY

In meeting the described challenges, the claimed invention first provides purification cartridges, comprising a reaction chamber comprising a sample loading inlet, the reaction chamber being capable of tolerating an internal temperature of at least about 95° C., an internal pressure of at least about 5 psi greater than ambient atmospheric pressure, or both; a molecular capture chamber comprising a molecular capture material and an elution tip capable of tolerating an internal temperature of at least about 95° C., the molecular capture chamber being moveable between a first position wherein a first connector places the molecular capture chamber in fluid communication with the reaction region and a second position wherein a second connector places the molecular capture chamber in fluid communication with an elution fluid inlet.

Also provided are processing systems for concentrating and isolating cellular components, comprising a plurality of cartridge receivers, at least one receiver being capable of maintaining a user-filled purification cartridge in a position to receive reaction fluid and elution fluid, at least one cartridge receiver comprising a thermal device capable of heating a molecular capture region on the purification cartridge to above about 40° C., or cooling the molecular capture region to below about ambient temperature, or both; and a fluid conduit capable of being fluidically connected to a sample loading inlet on a purification cartridge residing in a cartridge receiver, a elution fluid conduit, capable of being fluidically connected to an elution inlet on a purification cartridge; at least one collection vessel that receives fluid from a purification cartridge disposed in a cartridge receiver; and a controller that modulates fluid delivery to at least one purification cartridge disposed in a cartridge receiver, the system being capable of isolating one or more cellular components in assay-ready form in less than about 40 minutes.

Additionally provided are processing systems, comprising a plurality of cartridge receivers, at least one receiver being capable of maintaining a purification cartridge in a position to receive cell-containing sample fluid and an elution fluid, at least one cartridge receiver comprising a thermal device capable of heating a molecular capture region on the purification cartridge to above about 40° C., cooling the molecular capture region to below about 10° C., or both; and a fluid conduit capable of being fluidically connected to a sample loading inlet on a purification cartridge residing in a cartridge receiver, a elution fluid conduit, capable of being fluidically connected to an elution inlet on a purification cartridge; at least one collection vessel that receives fluid exiting a purification cartridge disposed in a cartridge receiver; and a controller that effects processing of two or more different samples disposed in two or more purification cartridges disposed in two or more cartridge receivers.

Further provided are processing systems, comprising a plurality of cartridge receivers, at least one receiver being capable of maintaining a purification cartridge in a position to receive cell-containing sample fluid and an elution fluid, at least one cartridge receiver comprising a thermal device capable of heating a molecular capture region on the purification cartridge to above about 65° C., cooling the molecular capture region to below about 10° C., or both; and a fluid conduit capable of being fluidically connected to a sample loading inlet on a purification cartridge residing in a cartridge receiver, an elution fluid conduit, capable of being fluidically connected to an elution inlet on a purification cartridge; at least one collection vessel that receives fluid exiting a purification cartridge disposed in a cartridge receiver; and a controller that effects sequential processing of two or more different samples disposed in two or more purification cartridges disposed in two or more cartridge receivers.

Also provided are processing systems, comprising a plurality of cartridge receivers, at least one receiver being capable of maintaining a purification cartridge in a position to receive cell-containing sample fluid and an elution fluid, at least one cartridge receiver comprising a thermal device capable of heating a molecular capture region on the purification cartridge to above about 65° C., cooling the molecular capture region to below about 10° C., or both; and a fluid conduit capable of being fluidically connected to a sample loading inlet on a purification cartridge residing in a cartridge receiver, a elution fluid conduit, capable of being fluidically connected to an elution inlet on a purification cartridge; at least one collection vessel that receives fluid exiting a purification cartridge disposed in a cartridge receiver; and a controller that effects simultaneous processing of two or more different samples disposed in two or more purification cartridges disposed in two or more cartridge receivers. In some embodiments, the system warms an elution fluid before the fluid is introduced to the elution inlet.

Further provided are methods of processing cellular samples, comprising (a) introducing a cell-containing sample to a reaction chamber of a purification cartridge; (b) liberating the contents of at least a portion of the cells in the sample by heating the sample in the reaction chamber to a temperature in the range of from about 100° C. to about 150° C. at a pressure greater than ambient pressure, by contacting the sample in the reaction chamber with one or more reagents, or both; (c) capturing at least a portion of the liberated cell contents by contacting the liberated cell contents to a molecular capture material in fluid communication with the reaction chamber that binds at least a portion of the cell contents; (d) interrupting the fluid communication between the reaction chamber and the molecular capture material and placing the molecular capture material in fluid communication with an elution fluid; (e) eluting at least a portion of the captured cell contents by contacting the capture material with an elution fluid, with heat, or any combination thereof; and (f) collecting at least a portion of the eluted cell contents.

Also provided are automated systems for isolating assay-ready cellular components, comprising a plurality of cartridge receivers, at least a portion of the receivers being capable of receiving a user-filled sample cartridge, at least one of the receivers capable of effecting a temperature of at least about 90° C., of less than about ambient temperature, or both, in a portion of the sample cartridge the system being capable of isolating one or more cellular components of a biological sample, in assay-ready form, in less than about 120 minutes.

Further provided are methods for the automated extraction, isolating, and purification of cellular components, comprising extracting cellular components from a cell-containing sample disposed in a sample cartridge by controllably heating the cell-containing sample to a temperature in the range of from about 15° C. to about 125° C., contacting the cell-containing sample with one or more reagents, or both; isolating a cellular component by contacting the extracted cellular components to a molecular capture material that binds at least a portion of the cell contents; purifying a cellular component by eluting at least a portion of the bound cellular components by contacting the capture material with an elution fluid, by heating the capture material, or any combination thereof; and collecting at least a portion of the eluted cellular components.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 4 is a table that identifies the various labeled elements shown in FIG. 2 and FIG. 3;

FIG. 7 is a table that identifies the various labeled elements shown in FIGS. 8 and 9;

FIG. 11 compares standard lysing chemistries against spin column-format lysing techniques;

DETAILED DESCRIPTION OF ILLUSTRATIVE EMBODIMENTS

Figure 1:
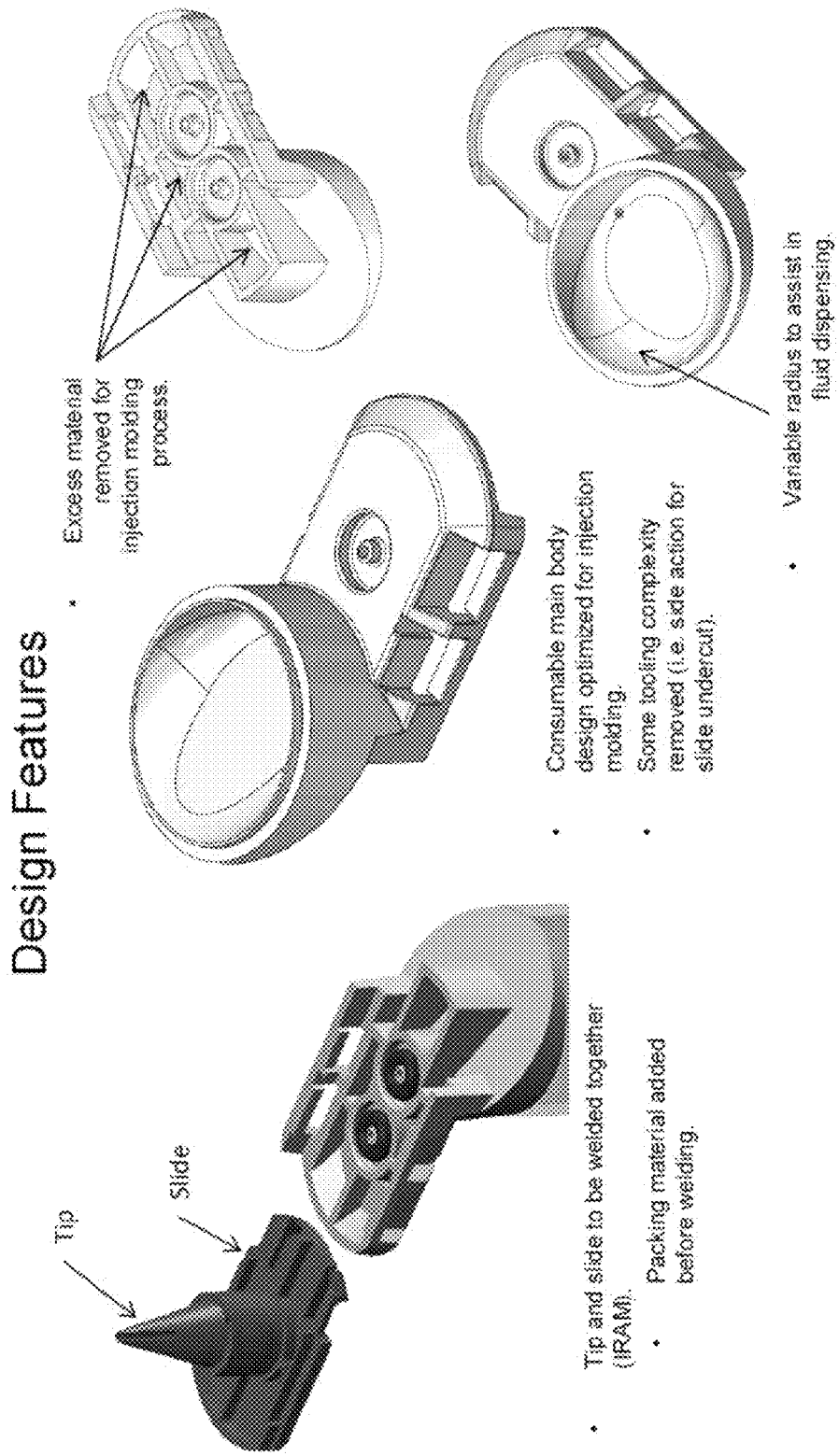
FIG. 1 depicts a non-limiting embodiment of the claimed invention, showing one possible orientation of the molecular capture region (shown as conical in the figure) within a purification cartridge.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In a first aspect, the claimed invention provides purification cartridges. A cartridge suitably includes a reaction chamber that itself includes a sample loading inlet. The reaction chamber is suitably capable of withstanding a temperature of at least about 95° C. or more; as described elsewhere herein, the cartridges may operate at room temperature or at even greater temperatures. The reaction chamber is also suitably capable of withstanding or operating at an internal pressure of at least about 5 psi greater than ambient atmospheric pressure.

The reaction chamber may be cylindrical in configuration, but may also be domed, conical, spherical, or virtually any other hollow shape. The reaction chamber is suitably capable of withstanding a temperature of at least about 140° C., an internal pressure of at least about 80 psi greater than ambient atmospheric pressure, or both. In some embodiments, the reaction chamber withstands temperatures of at least about 170° C. The chamber may withstand a pressure of 100 psi greater than ambient pressure, 150 psi greater than ambient pressure, 200, 250, 350, or even about 500 psi greater than ambient pressure. The chamber suitably operates at 20, 25, 30, 50, 75, 100, or 150 psi greater than ambient pressure, but higher pressures are within the scope of the claimed invention.

The reaction region is suitably capable of being positioned proximally adjacent to an external heater. The cartridges suitably include a molecular capture chamber that includes molecular capture material. The capture chamber may also include an outlet, which outlet may be characterized as an elution tip. The capture chamber is suitably capable of withstanding a temperature of at least about 95° C. Systems used with the cartridges may generate internal temperatures for the cartridges of 30 deg. C., 50 deg. C., 70 deg. C., 100 deg. C., 130 deg. C. and even higher in some embodiments; the cartridges are suitably constructed so as to tolerate such temperatures. The cartridges are suitably constructed to tolerate external temperatures of 50 deg. C., 75 deg. C., 100 deg. C., or even 150 deg. C. or 200 deg. C. Such external temperatures may be reached so as to achieve a desired internal temperature.

In some embodiments, the molecular capture chamber is moveable between a first position, in which a connector places the molecular capture chamber in fluid communication with the reaction region. The capture region is also suitably moveable to a second position, in which position a connector places the molecular capture chamber in fluid communication with an elution fluid inlet. The capture region may be moveable between two or more positions, so as to enable the dispensing or connection to a variety of downstream processes. The elution buffer may be delivered at a variety of temperatures; it may be delivered at below-ambient temperature, ambient temperature, or even at above ambient temperature. Elution buffer delivered at about 65 deg. C. is considered especially suitable. In some embodiments, the cartridge is constructed such that two or more capture chambers may be placed into fluid communication with the reaction chamber. The cartridge may also be constructed such that the reaction chamber is moveable between two or more positions.

The cartridge may be constructed such that the reaction chamber does not permit fluid to leave until the capture chamber is slid underneath the reaction chamber. In this way, the user may perform mixing, pressurizing, heating/cooling, and any other pressure steps on material contained within the reaction chamber while that fluid is in isolation from other components of the cartridge. In such embodiments, processing steps are performed in the reaction chamber while the capture chamber is in the elution position (i.e., is not in fluid communication with the reaction chamber), the capture chamber is then slid into fluid communication with the reaction chamber and the processed sample is then contacted to the capture material via, e.g., pressurized transport or other washing from the reaction chamber to the capture chamber. The capture chamber is then slid to what may be termed the elution position, where is no longer in fluid communication with the reaction chamber and is in fluid communication with an inlet (shown by "Elution Inlet" in FIG. 5), where elution fluid is flowed into the capture chamber to liberate target material that has bound to the capture material. In such embodiments, the reaction chamber is thus configured to contain fluids unless the capture chamber is positioned beneath it. This fluid containment can be effected by, e.g., a O-ring valve or other valve that remains closed until the capture chamber is slid underneath the valve to place the valve in an open position.

An exemplary, non-limiting embodiment of a purification cartridge 101 is shown in FIG. 1. In that embodiment, the molecular capture chamber 103 (conical region shown at the left side of figure) includes a tip 105 for eluting bound lysis products, and a tip for facilitating the elution of these products to a collector. As shown in the figure, the capture region (or chamber) is slidably mounted on the body of the purification cartridge, thus enabling the capture chamber to be placed first in fluid communication with the reaction chamber or sample vessel 107 (fully shown in FIGS. 2, 3, and 5) where lysis and filtering of a sample takes place. The capture chamber then receives the filtered lysis products, and captures the desired products. This can be accomplished by using a capture material 109 (shown in FIG. 33) in the capture chamber that selectively binds certain lysis products.

The capture chamber may then be slid to a second position where the capture chamber is no longer in fluid communication with the reaction chamber and is instead in fluid communication with a source of fluid, such as a buffer (not shown). The buffer is then suitably introduced to the capture chamber, with the buffer and processing conditions being chosen so as to elute the desired molecules from the capture chamber. As described elsewhere herein, capture material 109, such as silica, is suitably disposed within the capture chamber 103. In other embodiments not shown the chamber may be slid to a plurality of locations so as to place the capture chamber in fluid communication with multiple reaction chambers or other process modules.

Figure 2:
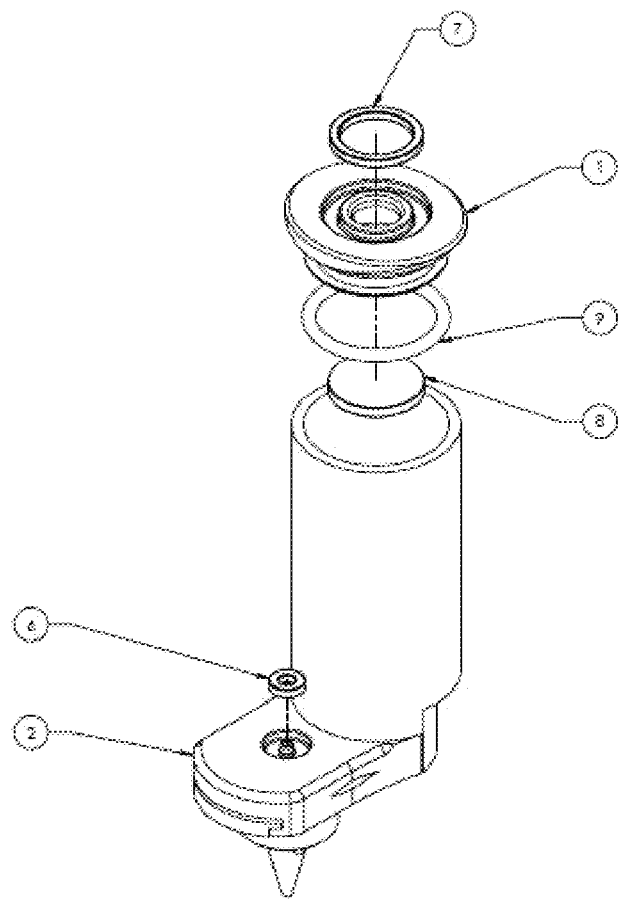
FIG. 2 depicts an exemplary embodiment of the claimed invention, showing one possible configuration for a reaction chamber.

FIG. 2 shows a component view of one embodiment of a reaction chamber. As shown in the figure (and by FIG. 4, which is a table that identifies the various elements of non-limiting FIGS. 2 and 3), the capture region may be modular, and include multiple components and seals. In this figure, the reaction chamber is shown mated to the body of a purification cartridge. At the lower left of the figure, a conical capture chamber is shown extending downward from the purification cartridge.

Figure 3:
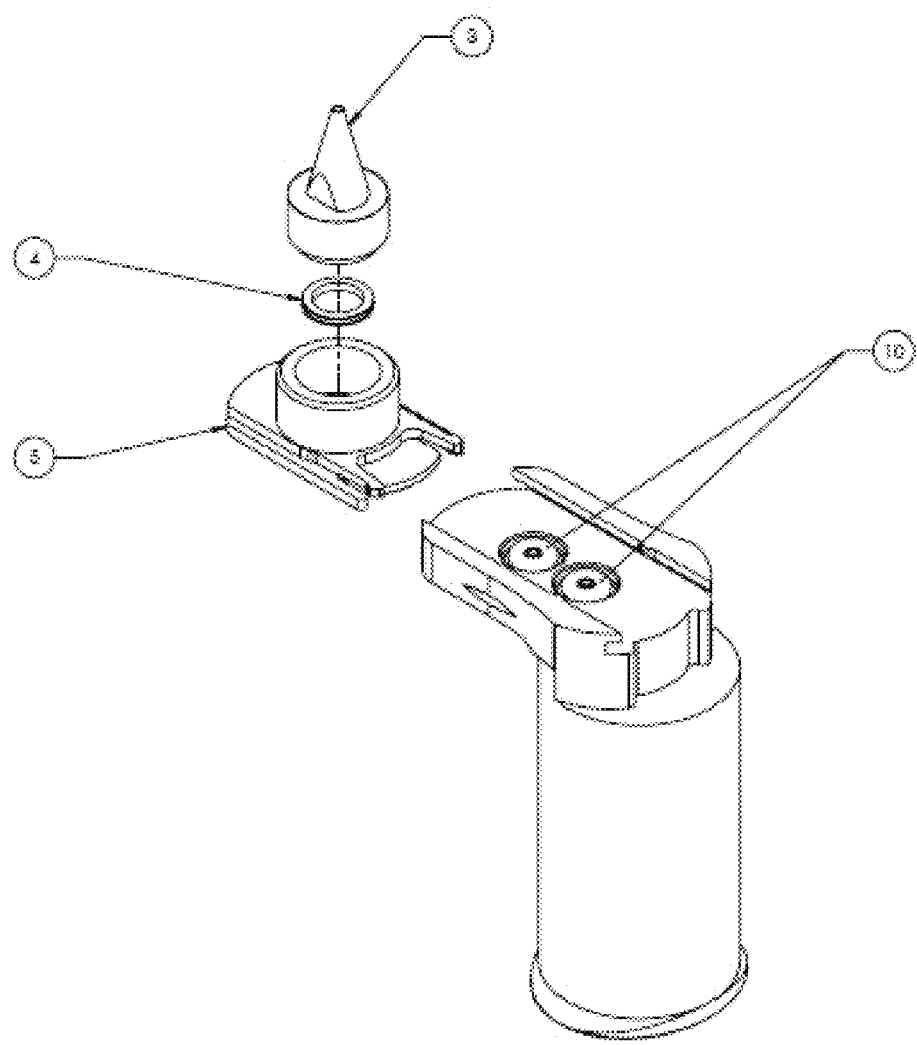
FIG. 3 depicts an alternative view of the device of FIG. 2, showing one possible orientation of the molecular capture region (shown as a conical configuration) relative to the remainder of the purification cartridge.

FIG. 3 depicts an alternative view of the device of FIG. 2. In this view, the conical capture region and elution tip (3) are shown mated via a compression ring (4) to a sliding portion (5) of the purification cartridge. As shown in the figure, the cartridge includes O-rings (10) that seal the fluidic path from the reaction chamber and the elution path to the slider and capture region.

Figure 5:
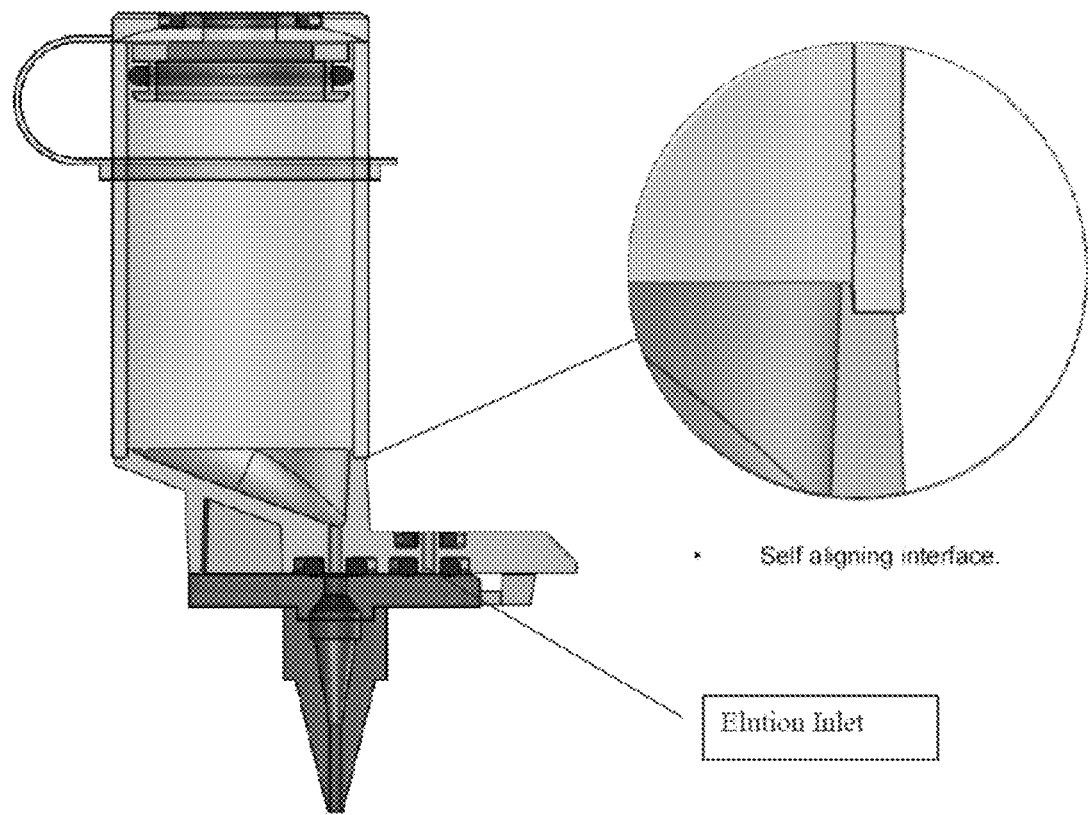
FIG. 5 depicts a cutaway view of a purification cartridge according to the claimed invention, with a magnified view of a self-aligning interface between a cylindrical reaction region and the body of the purification cartridge.

FIG. 5 depicts a cutaway view of an exemplary embodiment of the invention. At the bottom of the figure is shown a conical elution tip 105, with the inner conduit of the tip visible by way of the cutaway view. The left side of the figure contains the sample vessel 107 including the reaction chamber, which chamber is in fluid communication with the capture chamber 103 and elution tip. At the top of the reaction chamber is a sealing cap. In this figure, the cap is joined to the reaction chamber by a collar, although this is not necessary. The cap may include a sealing ring to maintain sealing against the exterior environment. The cap may also include a disc or other body that the user may actuate (e.g., via magnetic field) so as to effect mixing of the contents of the reaction chamber. The right side of the figure depicts an exemplary self-aligning interface between the reaction chamber and the body of the purification cartridge, which interface simplifies the attachment (and alignment) of the reaction chamber to the purification cartridge. This interface may be secured by tight physical contact between the reaction chamber and the cartridge body, by adhesive, sonic welding, solvent bonding, or even by infrared welding ("IRAM") techniques.

As shown in the cutaway view of FIG. 5, the capture chamber (and elution tip) may be slid (not shown) to the right so as to interrupt their fluid communication with the reaction chamber and to place them in fluid communication with an elution port 111 disposed on the right hand side of the purification cartridge body.

Samples that are analyzed by the claimed cartridges may be naturally derived (e.g., blood or plasma). Samples may also be synthetically derived. Samples may include nucleic acids, amino acids, carbohydrates, salts, polysaccharides, and the like.

In some embodiments, the cartridge includes a sample cap that prevents fluid flow across the sample inlet into (or out of) the reaction region. Such a cap is shown by element (1) in FIG. 1, and also at the upper left of FIG. 5, where the cap is shown attached to the body of the reaction region by a C-shaped connector. The cap may be closed by a disk, and also suitably includes an O-ring or other sealer to seal during application of positive or negative pressure to the reaction region of the cartridge. In some embodiments, the sample cap permits fluid flow into or out of the reaction region when subjected to a pressure differential, and prevents such flow when the cap is not subjected to a pressure differential.

The cartridges suitably include a disc or other body (e.g., bar, cube, doughnut, and the like) that can be disposed within the reaction region of the cartridge. This body is suitably made of a metal or other material (e.g., a magnetic material) that can be actuated by application of a magnetic field. In this way, the user applies a magnetic field to the body so as to cause the body to move, thus mixing the contents of the reaction region. The magnetic field may be intermittent, oscillating, alternating, or otherwise configured so as to effect motion of the body that results in the mixing of the contents of the reaction region.

In some embodiments, the systems use addition of a chaotropic buffer and the addition of alcohols to facilitate the precipitation of the liberated nucleic acids. To achieve effective mixing, the system makes use of a magnetic disk, that when rotated creates a vortex effect in the sample preparation chamber.

Increasing the speed of the magnetic disk rotation particularly enhanced the yield. Increasing the duration of the mixing step resulted in DNA extraction of an equivalent yield compared to bench top protocol for the extraction of comparatively large volume (e.g., 1.0 ml) blood samples. Additional information is included in "A completely automated sample preparation instrument and consumable device for isolation and purification of nucleic acids," by West et al., submitted March 2010 to the *Journal of the Association for Laboratory Automation* (on file with prosecution counsel), the entirety of which is incorporated herein by reference.

A filter is, in some embodiments, also suitably disposed within the reaction region of the cartridge or even in or adjacent to the outlet of the reaction region. Suitable filters are of sufficient area to be able to filter, without clogging, up to about 100,000,000 lysed cells, up to about 1 ml of liquid, up to about 50 mg of tissue, or any combination thereof, disposed in the capture chamber. Filters capable of filtering $1 \times 10^8$ lysed bacterial cells without clogging are considered especially suitable. The cartridges suitably process 1 ml of blood, which may contain from about 4.9 billion to about 5.5 billion red blood cells. In some embodiments, the filter is capable of processing 10 billion, 15 billion, or even up to 25 billion cells before clogging. A filter is not necessary, however, to the functioning of the claimed invention. In some embodiments, the invention is configured so as to process pre-filtered samples.

The capture region suitably includes an outlet. Such outlets may be characterized as being tapered elution tips, such as the tip shown in FIG. 1. Such tips are suitably characterized as being tapered to an opening smaller in cross-sectional dimension relative to the corresponding cross-sectional dimension of the elution tip's connection with the molecular capture region. The tip may be in the form of a pipette tip or a capillary column. The capture region, elution tip, or both suitably have an internal volume in the range of from about 20 microliters to about 100 microliters, or from about 20 microliters to about 40 microliters. The elution tip is suitably capable of delivering fluid (e.g., purified, eluted target material) to a sample collection vessel. The capture chamber may also include a capillary or capillaries; which capillaries may include silica or porous polymer monoliths.

The capture material disposed within the capture region is suitably in the form of a disk, a plug, a frit, a monolith, a bead, a column, and the like. Suitable materials include, inter alia, silica, polyethylene, polycarbonate, acrylate polymer, methacrylate polymer, cellulose, hydrogels, and the like. The capture material is suitably chosen or adapted to bind to an amino acid, a protein, nucleic acid, a polysaccharide, and the like—the material optimally binds to cellular component (e.g., nucleic acid) that the user seeks to isolate.

The elution inlet is suitably capable of being fluidically connected to a fluid source exterior to said purification cartridge. In one exemplary embodiment, the elution inlet is coupled to a source of elution fluid, such as a buffer, which fluid is then exerted into the capture chamber so as to elute target material that has bound to the capture material. The capture region is suitably capable of tolerating a temperature of at least about 95° C., or at least about 140° C., or up to about 170 deg. C., as may be limited by the materials used in the devices. In some embodiments, the capture region is capable of tolerating a temperature of less than ambient temperature, or less than about 20 deg. C., or less than about 15 deg. C. or even at less than about 10 deg. C. The capture region may include an irremovable region that is integral to the purification cartridge, or be removable from the cartridge, or both.

The capture material suitably includes a material, device, or both, capable of selectively capturing one or more types of molecules that enter the capture region. Microarrays, porous polymer monoliths, silica membrane, cellulose packing materials, polycarbonate membranes, and sequencing flow cells (e.g., those made by the Illumina corporation), are all considered suitable capture materials.

The cartridge is suitably configured such that the capture region is capable of being positioned adjacent to an external heater, an external cooler, or both. The cartridge may include valves, conduits, and the like that are in fluid communication with the sample inlet, the reaction region, or the molecular capture region. Such fluidic structures enable the user to modulate fluid flow into, within, and out of the cartridge. The cartridges may also include reagents disposed within, including enzymes, nucleic acids, proteins, acids, bases, aliphatic solvents, cyclic alkanes, polycyclic alkanes, cycloalkenes, polycylcic alkenes, glycerol, detergents, chaotropic agents, alcohols, and the like. Such reagents may be useful in effecting cell lysis or other processes, and are suitably stored on or in the device into which the cartridge is mated.

In operation, the present invention provides a chamber that accommodates lysing processes as well as other reactions, as the sample and any reagents may be contacted with one another in, for example, the chamber (e.g., cylindrical structure shown between items (2) and (8) in FIG. 2). This presents particular advantages, as this configuration allows for serial addition of samples and reagents or other chemistries to one another. It also allows for an essentially homogenous reaction mixture. So-called flow-through systems, however, lack these advantages.

For example, in flow-through systems, the sample is not necessarily homogenous, as sample material that initially passes through a flow channel for processing may not be the same as sample material that is in the central flow portion. Thus, flow-through systems may provide different results depending on whether the system is analyzing sample that first passes through the system or analyzes sample that passes through the system at a later time. For example, in a flow-through system, the composition of the fluid that contacts a capture material may not be consistent. A sample fluid that is flowed into a capture material may start out as being mostly buffer or mostly reagent, and then become mostly sample, and then transition again to a buffer- or reagent-rich region of flow. Thus, flow-through systems face challenges in delivering consistent-composition fluids to capture materials or other process modules, which can reduce the effectiveness or accuracy of such systems.

Flow-through systems also require priming, which creates additional complications. In addition, flow-through systems require careful control of flow rate and temperature to achieve consistent processing; the bolus-based processes of the claimed invention do not necessarily require such control. Flow-through systems also pose challenges to chemical-based sample preparation techniques, as addition and sufficient mixing of chemical reagents is difficult to achieve in a flow-through system, particularly those systems that are composed of small chambers linked by narrow flow tubes.

In addition, flow-through systems require microfluidic manufacturing techniques, which techniques may complicate the manufacture and use of the systems and their associated components. Microfluidic systems are also limited in the sample volumes they can process; the claimed invention is capable of handling volumes of 5 ml, 7 ml, or even up to about 10 or 15 ml of combined reagents and sample. The claimed invention also decouples sample preparation steps (e.g., lysing) from detection steps, which cannot be realized by flow-through systems, which systems characteristically have sample preparation (e.g., lysing) in direct, continuous fluid communication with downstream detection steps or other post-processing (e.g., PCR). Such flow-through systems, however, run the risk of permitting downstream (or upstream) contamination. By contrast, decoupling the sample preparation from the detection allows the user to effect sample preparation steps without affecting downstream steps.

Flow-through systems also spilt or diverge a single flow path into two or more separate streams. This splitting, however, can create the potential for undesirable backflows or even contamination between streams. The claimed invention avoids such complications by—as shown in FIGS. 1, 2, 3, and 5—suitably incorporating a slider that creates two separate flow paths not capable of fluidic communication with one another.

Other systems include combining sample material with a solid phase material and reagents to effect processing, followed by purifying the solid phase with target material bound thereto and further separating the target material from the solid phase. The claimed invention suitably operates in a qualitatively different way; as described, processing occurs in a reaction chamber spatially separate from the capture chamber.

The present invention also provides processing systems for concentrating and isolating cellular components. These systems suitably include a plurality of cartridge receivers, at least one receiver being capable of maintaining a user-filled purification cartridge in a position to receive reaction fluid and elution fluid, at least one cartridge receiver comprising a thermal device capable of heating a molecular capture region on the purification cartridge to above about 40° C., or cooling the molecular capture region to below about 10° C., or both; and a fluid conduit capable of being fluidically connected to a sample loading inlet on a purification cartridge residing in a cartridge receiver, a elution fluid conduit, capable of being fluidically connected to an elution inlet on a purification cartridge; at least one collection vessel that receives fluid from a purification cartridge disposed in a cartridge receiver; and a controller that modulates fluid delivery to at least one purification cartridge disposed in a cartridge receiver. It is not necessary that the systems include a cooler, and the systems may operate at about ambient temperature, in some embodiments. In others, the system may cool the reaction chamber, the capture chamber, or even one or more fluids introduced to the reaction chamber, the capture chamber, or both.

The systems are suitably capable of isolating one or more cellular components in assay-ready form in less than about 120 minutes, less than about 60 minutes, or even less than about 20 minutes or about 10 minutes.

The systems suitably include a waste fluid collection receptacle or an elutant fluid receptacle. Such receptacles may be stationary or moveable, and are suitably adapted or positioned to receive a waste fluid exiting from an elution tip into the waste fluid receptacle, or to receive elution fluid emanating from said elution tip.

Systems according to the claimed invention also suitably include a thermal device capable of heating the molecular capture region on the purification cartridge to at least about 50 deg. C., 75° C., at least about 90° C., at least about 150, 250, or even up to about 500° C., as may be limited by the materials of the devices and cartridges. Temperatures of 35 deg. C., 50 deg. C., or even 100 deg. C. are considered especially suitably. A thermal device may also be used to cool the molecular capture region to less than ambient temperature, although such coolers are not necessary.

The systems also suitably include a scanner that reads identifying information displayed on a cartridge or within the cartridge. As one non-limiting example, the system may include a scanner that reads a bar code displayed on a cartridge, which bar code includes information about the sample contained within the cartridge that can be used by the system to effect processing steps (including reagent delivery) that are suitable for the sample contained within the cartridge and that is suitable for isolating the desired material from that sample.

In a particularly suitable embodiment, the scanner may be used to determine the contents of a particular sample disposed in a purification cartridge, which information can then be used to set the schedule of processing steps to be applied to that sample. The scanner may be disposed in such a way that the user scans a sample before the cartridge is inserted into the system, or may be disposed within the system so that the system registers a barcode, RFID chip, or other identifying information on a cartridge when the cartridge is inserted or at some other time before the cartridge is processed. It is contemplated that the user may also input to the system information regarding the sample or samples that are to be processed. In some embodiments, the information associated with a cartridge is used to select one or more processing steps to be performed on the cartridge.

Figure 6:
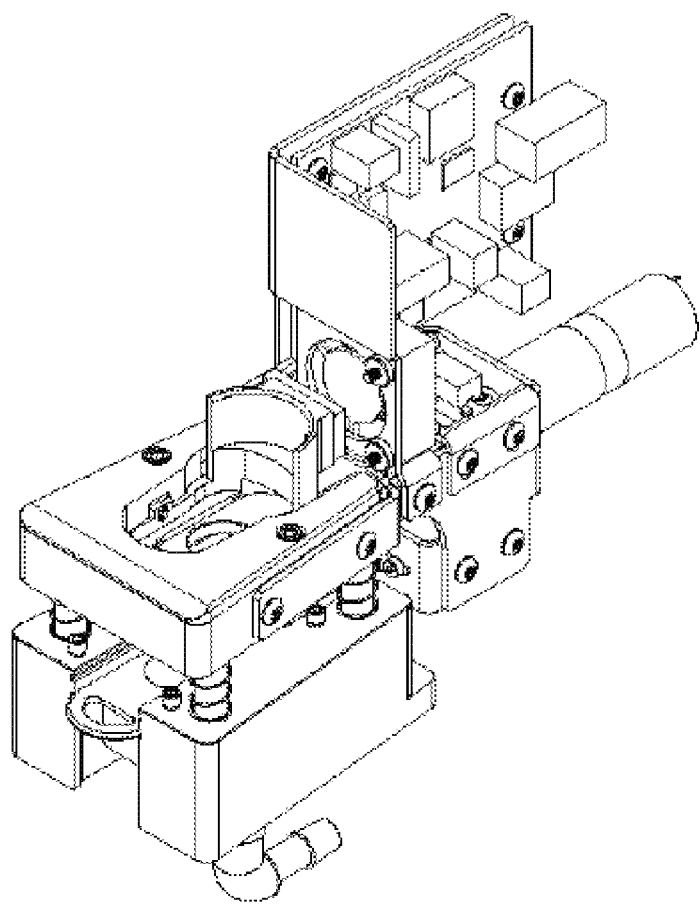
FIG. 6 depicts an exemplary system that receives a purification cartridge according to the claimed invention.

Slots, holes, or other recesses may be present in the systems to receive the purification cartridges and maintain the cartridges in proper position. One such receiving slot is shown in FIG. 6, where, at the left of the figure, a slot is shown for receiving a purification cartridge into the system. The cartridges may be secured by magnetic bodies, by spring-loaded grips, and the like.

The systems also suitably include a supply of elution buffer in fluid communication with an elution fluid conduit. This conduit is suitable adapted to place the elution buffer (or fluid) in fluid communication with the capture region of a cartridge engaged with the system.

Figure 14:
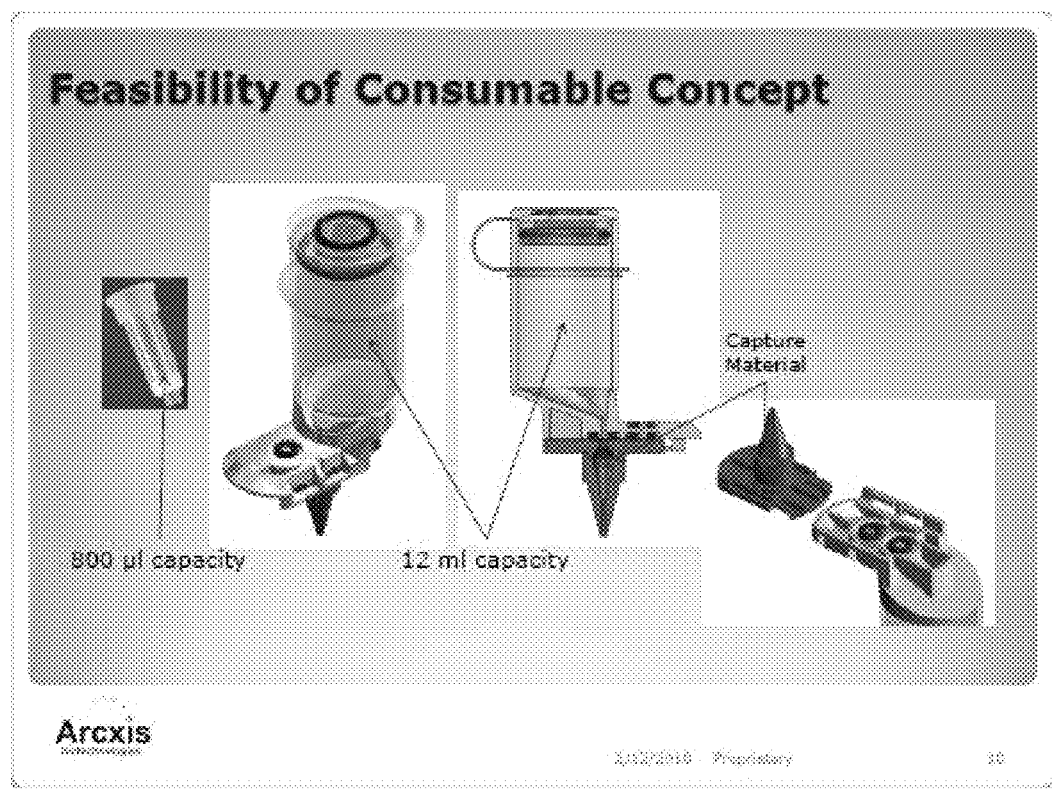
FIG. 14 depicts an exemplary embodiment of the claimed invention.

The controller or controllers of the system are suitably capable of modulating the delivery of one or more fluids to two or more purification cartridges disposed in cartridge receivers. For example, the controller modulates the introduction of buffer or lysing reagents into the reaction region, where such materials interact with the sample disposed in the reaction region. The controller may also control the movement of the capture chamber from a position where the region is in fluid communication with the reaction chamber to a second position where the capture region is in fluid communication with an inlet for the elution fluid; as shown in FIG. 14, the capture region may be moved between positions. A controller may also modulate the mixing (via application of a magnetic field to a metallic or magnetic body in the reaction region) of fluids present in the reaction chamber by effecting mechanical mixing or stirring of the fluids. Mixing may also be effected by modulating the application or removal of thermal energy from fluid in the reaction chamber. The chamber may also be shaken, vortexed or even vibrated to effect mixing; in some embodiments, the fluid may be pumped or pressurized in an up/down or side/side manner to mix.

The system suitably includes one or more magnets or magnetic field generators that actuate magnetic bodies disposed within a purification cartridge disposed within that receiver. These are described in additional detail elsewhere herein.

The system is suitably is capable of modulating processing of two different samples at the same time, which modulation is suitably accomplished by a controller. The controller is suitably capable of modulating simultaneous processing of two or more different samples. In some embodiments, the controller is capable of modulating sequential processing of two or more different samples.

As one non-limiting example, the system may process several samples—which samples may be the same material (e.g., plasma) or different materials—simultaneously. In some embodiments, the system may be processing a first sample when the user introduces an additional sample, which sample the system begins to process while processing the first sample. These samples may be the same material (e.g., plasma) or different materials. The system may also be configured such that different targets (nucleic acids, proteins, and the like) are isolated from different samples. For example, the system could isolate nucleic acid from a sample of plasma while also isolating proteins from a blood sample.

The controller also suitably modulates fluid recovery from at least one purification cartridge disposed in a cartridge receiver. The receivers are suitably rotatably positioned, but may also be positioned in a linear fashion or even on a conveyor belt. The system is suitably configured such that the user may access different receivers.

Also provided are processing systems. These systems suitably include a plurality of cartridge receivers, at least one receiver being capable of maintaining a purification cartridge in a position to receive cell-containing sample fluid and an elution fluid. At least one cartridge receiver suitably includes a thermal device capable of heating a molecular capture region on the purification cartridge to at least about 40° C., cooling the molecular capture region to below about 10° C., or both. The systems also suitably include a conduit capable of being fluidically connected to a sample loading inlet on a purification cartridge residing in a cartridge receiver, an elution fluid conduit, capable of being fluidically connected to an elution inlet on a purification cartridge; at least one collection vessel that receives fluid exiting a purification cartridge disposed in a cartridge receiver; and a controller that effects processing of two or more different samples disposed in two or more purification cartridges disposed in two or more cartridge receivers.

The controller is suitably capable of effecting different processing steps for two or more samples disposed in two or more purification cartridges disposed in two or more cartridge receivers. For example, the system, modulated by one or more controllers, effects a lysing step in a first purification cartridge while effecting an elution step in a second purification cartridge. In this way, the system is capable of processing sample-containing cartridges on a rolling or random access basis.

Also provided are processing systems. These systems suitably include a plurality of cartridge receivers, at least one receiver being capable of maintaining a purification cartridge in a position to receive cell-containing sample fluid and an elution fluid, at least one cartridge receiver comprising a thermal device capable of heating a molecular capture region on the purification cartridge to above about 40° C., cooling the molecular capture region to below ambient temperature or even below about 10° C., or both; and a fluid conduit capable of being fluidically connected to a sample loading inlet on a purification cartridge residing in a cartridge receiver, a elution fluid conduit, capable of being fluidically connected to an elution inlet on a purification cartridge; at least one collection vessel that receives fluid exiting a purification cartridge disposed in a cartridge receiver; and a controller that effects simultaneous processing of two or more different samples disposed in two or more purification cartridges disposed in two or more cartridge receivers.

The system suitably performs different processing steps for two or more of two or more samples disposed in two or more purification cartridges disposed in two or more cartridge receivers. For example, the system may simultaneously perform lysing steps for two or more samples in two or more purification cartridges simultaneously.

Also provided are methods of processing cellular samples. These methods suitably include:

(a) introducing a cell-containing sample to a reaction chamber of a purification cartridge;

(b) liberating the contents of at least a portion of the cells in the sample by heating the sample in the reaction chamber to a temperature in the range of from about 100° C. to about 150° C. at a pressure greater than ambient pressure, by contacting the sample in the reaction chamber with one or more reagents, or both;

(c) capturing at least a portion of the liberated cell contents by contacting the liberated cell contents to a molecular capture material in fluid communication with the reaction chamber that binds at least a portion of the cell contents;

(d) interrupting the fluid communication between the reaction chamber and the molecular capture material and placing the molecular capture material in fluid communication with an elution fluid;

(e) eluting at least a portion of the captured cell contents by contacting the capture material with an elution fluid, with heat, or any combination thereof; and (f) collecting at least a portion of the eluted cell contents.

In some embodiments, the lysis is performed at or at about room temperature. In such embodiments, thermal control is not necessary. This is the case, e.g., where viral particles are isolated from blood. For gram-positive and gram-negative bacteria, lysis may be performed at around 95° C. at ambient pressure. In other embodiments, however, the reaction chamber may be processed up to 30 psi or more, and heating the region up to 150° C.

The methods include inserting the purification cartridge into a system capable of supplying fluid to the purification cartridge. Such systems are described elsewhere herein. Reagents suitable for the claimed methods include proteolytic enzymes, DNAses, RNAses, inhibitors, chaotropic salts, ionic salts, buffers, detergents, water, organic solvents, acids, bases, alcohols, and the like. Elution fluids suitable for the claimed methods include water, Tris-EDTA buffer, and the like.

In some embodiments, the user may agitate or mix the sample while the sample resides in the reaction chamber. Such mixing is described elsewhere herein in further detail.

The user suitably introduces two or more samples to two or more purification cartridges. The samples may include different biological fluids, such as blood, plasma, saliva, sputum, FFPE (formalin-fixed, paraffin-embedded) material, frozen tissue sections, CSF (cerebral spinal fluid), stool, water, environmental samples, vegetative tissue or cells, mammalian tissues and cells, cell free media solution, water, buffered sample, swab samples, saliva, sperm, vaginal discharge, amniotic fluid, tumor biopsy, bacterial cells, bacterial spores, viruses, fungi, protozoa, neonatal blood, and the like. Essentially any sample can be analyzed by the disclosed methods and systems.

The actuation of at least one of the aforementioned steps (a)-(f) is suitably modulated by a controller. In some embodiments, the performing steps (a)-(f) for the two or more samples is done essentially in parallel. In such embodiments, two or more samples are processed simultaneously. In other embodiments, steps (a)-(f) are performed for the two or more samples at different times. In such embodiments, a second sample begins processing after a first sample has begun processing; the samples are thus processed in a random access fashion. The reagents used in the processing of two or more samples may differ, the temperatures used in the processing of the two or more samples may differ, the elution fluids used in the processing of the two or more samples may differ. Thus, two or more samples may undergo different processing steps or be processed in different manners. For example, a sample comprising blood might be incubated at 60 deg. C. while a sample comprising water or other fluid might be incubated at 95 deg. C. at the same time.

Also provided are systems for isolating assay-ready cellular components. These systems suitably include a plurality of cartridge receivers, at least a portion of the receivers being capable of receiving a user-filled sample cartridge, at least one of the receivers capable of effecting a temperature of at least about 90° C., of less than about −10° C., or both, in a portion of the sample cartridge the system being capable of isolating one or more cellular components of a biological sample, in assay-ready form, in less than about 40 minutes.

One or more of the receivers is suitably capable of agitating the contents of the sample cartridge. The systems suitably isolate cellular components (e.g., proteins, nucleic acids) from two or more biological samples of different origins. The systems suitably isolate two or more different cellular components from biological samples of a common origin, but may also suitably isolate two or more different cellular components from biological samples of different origins. For example, the system may process samples from humans and animals at the same time. Alternatively, the system may process different kinds of samples (e.g., plasma and whole blood) at the same time.

The systems may include two or more reaction fluids that are introduced to two or more sample cartridges. Such reaction fluids may include water, buffers, lysing reagents, enzymes, and the like. The systems also suitably include two or more elution fluids that are introduced to two or more sample cartridges. In this way, different cellular materials are liberated from capture chambers by using different elution fluids.

The systems suitably include a controller that modulates fluid introduction, fluid removal, or both, from two or more sample cartridges residing in cartridge receivers. These actions may be effected by pumps, bladders, valves, pistons, and the like. Controllers may also be used to modulate temperature of two or more sample cartridges residing in cartridge receivers. The system is suitably capable of effecting different temperatures at two or more purification cartridges.

As described elsewhere herein, the systems are suitably capable of simultaneously processing multiple sample cartridges. In some embodiments, the systems process multiple samples on a rolling or random access basis, where a second sample is introduced and undergoes processing after a first sample's processing has already begun. The systems isolate one or more cellular components of a biological sample, in assay-ready form, in less than about 20 minutes, or even less than about 10 minutes.

Also provided are methods for the automated extraction, isolating, and purification of cellular components. These methods suitably include extracting cellular components from a cell-containing sample disposed in a sample cartridge by controllably heating the cell-containing sample to a temperature in the range of from about 15° C. to about 125° C., to about 150° C., or even about 170° C., depending on the materials used, contacting the cell-containing sample with one or more reagents, or both; isolating a cellular component by contacting the extracted cellular components to a molecular capture material that binds at least a portion of the cell contents; purifying a cellular component by eluting at least a portion of the bound cellular components by contacting the capture material with an elution fluid, by heating the capture material, or any combination thereof; and collecting at least a portion of the eluted cellular components.

A controller suitably effects one or more of these described method steps. The methods may be performed to effect collection of two or more cellular components from cell-containing samples of common origin, and may also be performed to effect collection of two or more cellular components (e.g., RNA and DNA) from two or more cell-containing samples of different origin. Alternatively, the methods may be performed to effect collection of a cellular component (e.g., RNA) from two or more cell-containing samples of different origin. Contacting the sample with one or more reagents, or both, may be effected at a pressure greater than ambient pressure. In some embodiments, the methods include initiating, at different times, at least one of the extraction, isolation, and purification performed on of two or more samples. In this way, the methods contemplate processing of different samples in a sequential manner, as additional samples are made available. In other embodiments, the user simultaneously initiates at least one of the extraction, isolation, and purification performed on two or more samples. In this way, the user may process two—or more—samples at essentially the same time.

FIG. 6 is an exemplary embodiment of a system capable of interacting with the purification cartridges of the claimed invention. A purification cartridge (not shown) is suitably inserted into the receiving slot depicted at the left side of the figure. The cartridge is securely seated in the receiving slot, and the sample inlet port of the cartridge is mated to a sample source. The cartridge may be secured in the system by a tab-and-slot configuration, by one or more pegs that fit into one or more holes, or by other securing mechanisms known to those of ordinary skill in the art.

Figure 8:
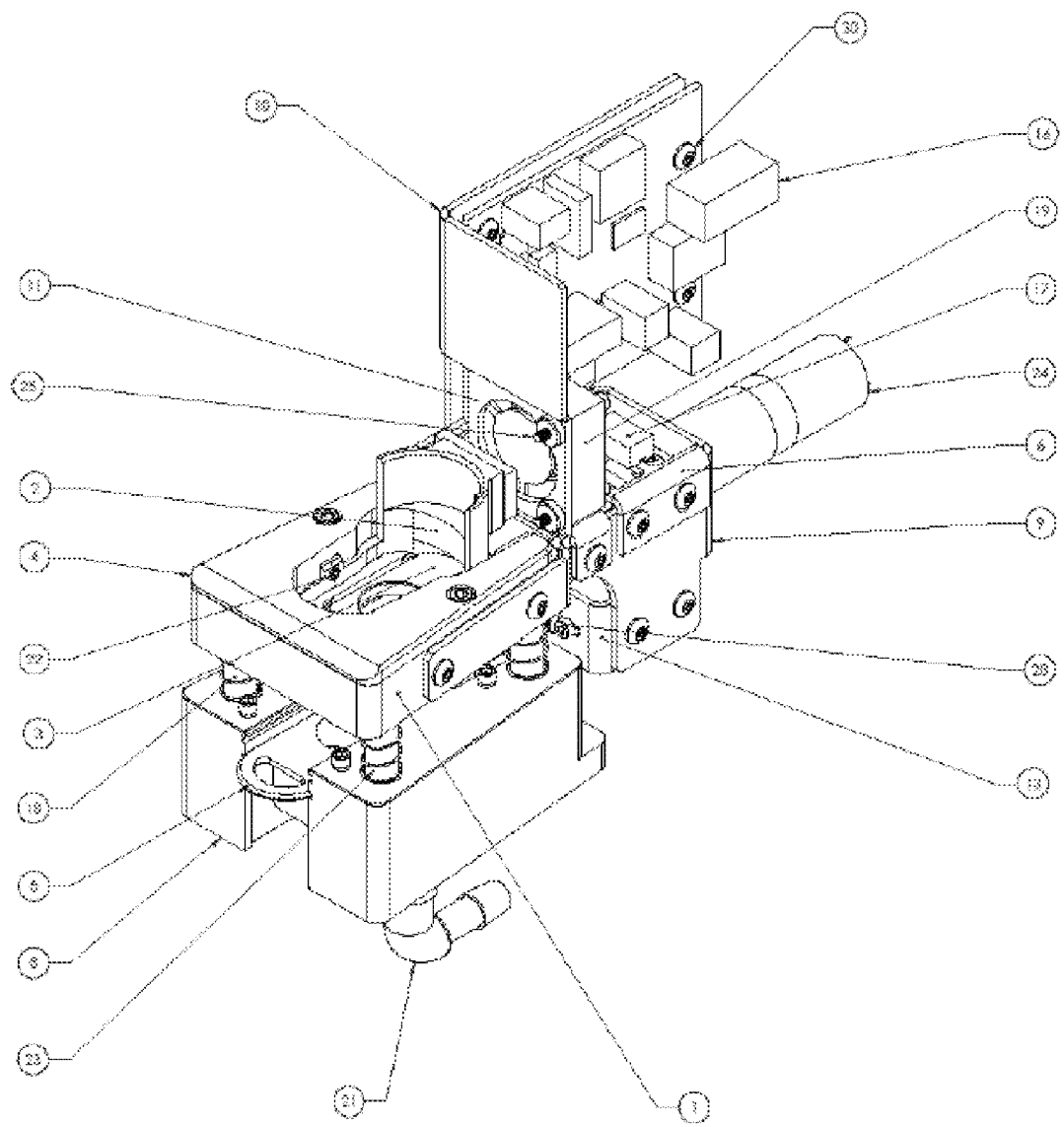
FIG. 8 depicts an exemplary system that receives a purification cartridge according to the claimed invention.
Figure 9:
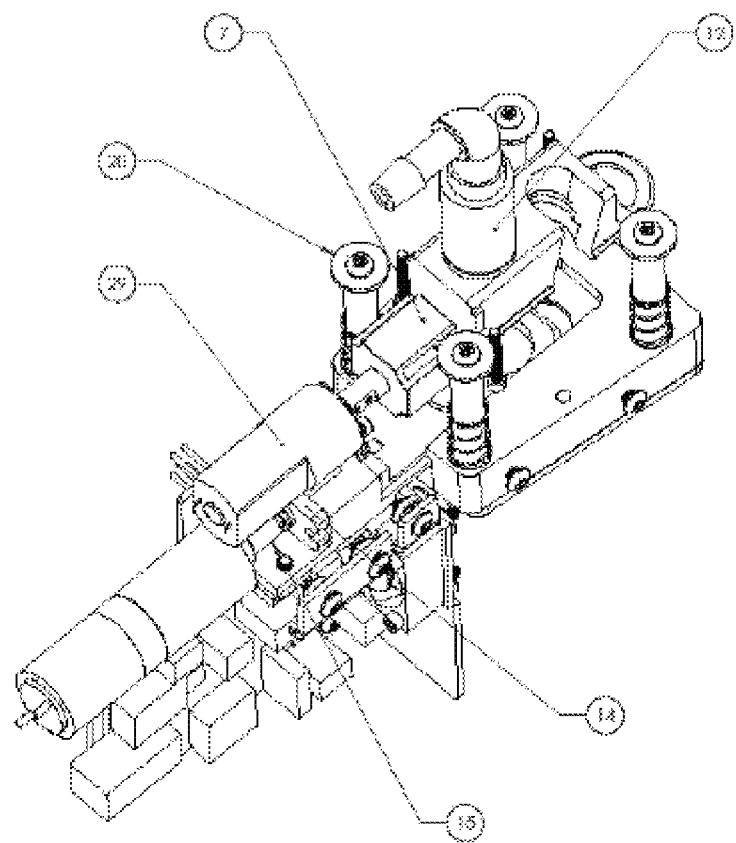
FIG. 9 is a further depiction of a system that interacts with a purification cartridge according to the claimed invention.

FIG. 7 is a table that lists the various elements shown in FIGS. 8 and 9.

FIG. 8 depicts a labeled view of a cartridge receiver 202 (part of the processing system 200 shown in FIG. 36) that interacts with a purification cartridge according to the current invention. The cartridge receiver 202 has a recess 204 configured to receive a purification cartridge 101. The cartridge receiver also has a motor 24 configured to actuate the capture chamber from a load position in which the capture material is in fluid communication with the sample vessel to an elution position, in which the capture material is in fluid communication with an elution port. The motor may be controlled by controller 16. The cartridge receiver also has a tube 21 extending therefrom. Mounting brackets (9), (10), and (11) are used to support the system. The thermal base (1) of the system suitably interacts with the cartridge, as does a thermal element (2) that is used to introduce (or withdraw) heat from the sample cartridge. A slide (3) is used to accommodate a capture chamber (described elsewhere herein), which can be positioned so as to be in fluid communication with a reaction chamber (not shown) and to be in fluid communication with an elution buffer inlet (not shown) and a collector or collection vessel (not shown). A cover (4) is used to shield the thermal base (1). A drawer (5) is incorporated into the body of the cartridge. In some embodiments, a sensor flag (6) is present. A magnet may be used to secure the cartridge to the system; a spring-loaded bracket may also be used.

FIG. 9 depicts an additional component view of a system that interacts with the cartridges of the claimed invention. The various elements are defined in FIG. 7.

Figure 10:
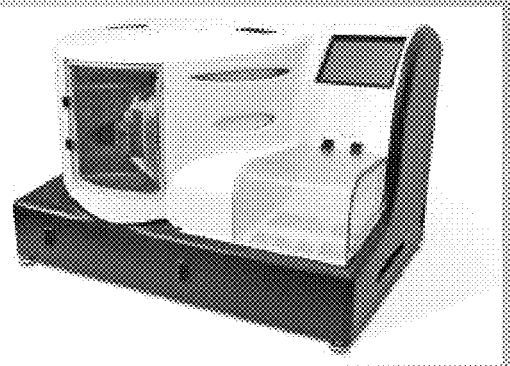
FIG. 10 is a non-limiting embodiment of the claimed invention.

FIG. 10 illustrates a non-limiting embodiment of the claimed invention. As shown, the invention is capable of analyzing up to 12 samples per sample run. The systems are, in some embodiments, capable of "walk away" operation, in which the user introduces the sample materials (suitably in purification cartridges) to the system and can "walk away" as the system executes the processing steps for the samples without user intervention.

FIG. 11 compares standard lysing chemistries—including chaotropic salts and silica membranes—with spin column techniques. (Spin columns are small columns packed with a gel filtration resin.) As shown, spin columns can be variable and require trained technicians, as contrasted with the "walk away" nature of the claimed invention.

Figure 12:
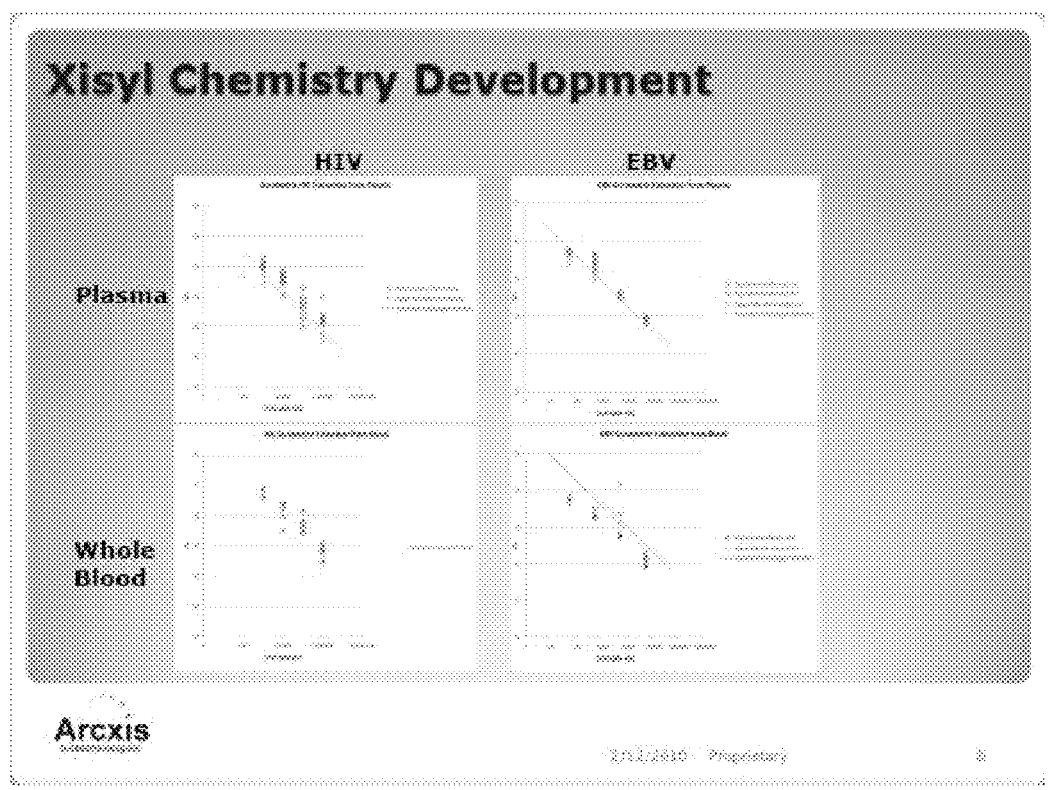
FIG. 12 illustrates results from testing HIV- and EBV-containing plasma and whole blood.

FIG. 12 depicts the development of the claimed invention's chemistry in the context of HIV and EBV assays.

Figure 13:
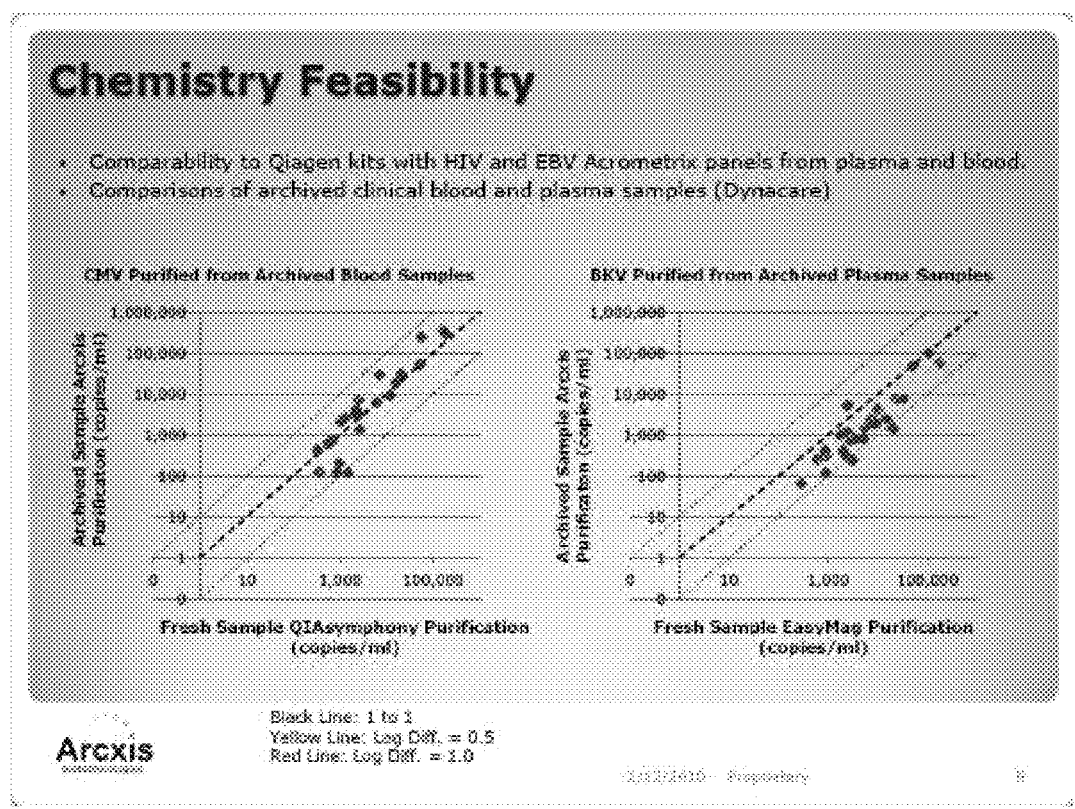
FIG. 13 illustrates a comparison between the claimed invention against a Qiagen® QiaSymphony and the Roche EasyMag compact product.

FIG. 13 demonstrates that analysis according to the claimed invention is comparable to existing Qiagen® products.

An alternative embodiment of the claimed invention is shown in FIG. 14. That figure—like FIG. 5—depicts a reaction chamber mounted on the body of a purification cartridge. Capture material is disposed within the capture chamber. As shown, the capture chamber may be position in fluid communication with the reaction chamber so as to receive molecules or other material produced by lysing cells (or otherwise processing a cellular sample). The capture chamber may also be positioned (e.g., by sliding) so as to interrupt its fluid communication with the reaction chamber, and to place the capture chamber in fluid communication with a source of elution fluid, such as a buffer. Suitable capture materials and elution fluids are described elsewhere herein. In other embodiments, the reaction chamber is positioned—after reaction product is introduced to the capture chamber—so as to interrupt the fluid communication between the reaction and capture chambers. In such embodiments, elution fluid is then introduced to the capture chamber so as to liberate material (e.g., molecules) that may be bound to the capture material.

Figure 15:
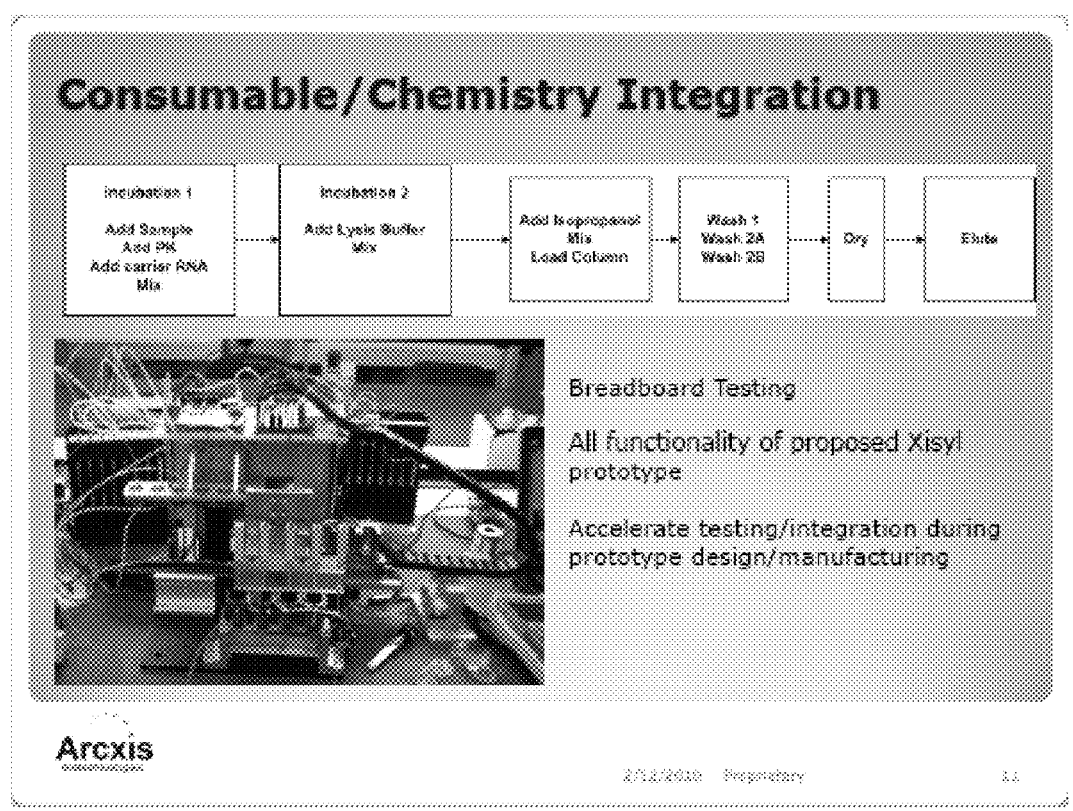
FIG. 15 depicts selected development steps of the claimed invention.
Figure 16:
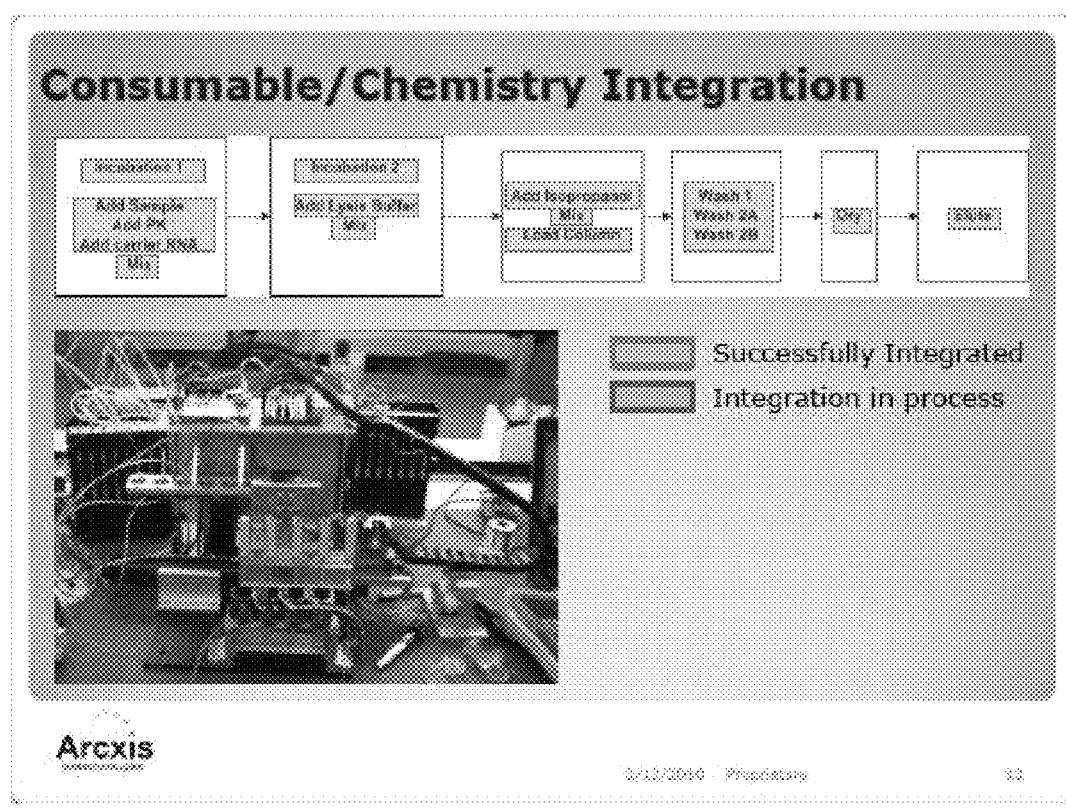
FIG. 16 depicts selected development steps of the claimed invention.

FIGS. 15-16 describe the integration between the chemistry (e.g., lysing) useful in the claimed invention and the consumable (i.e., purification cartridge) of the invention.

Figure 17:
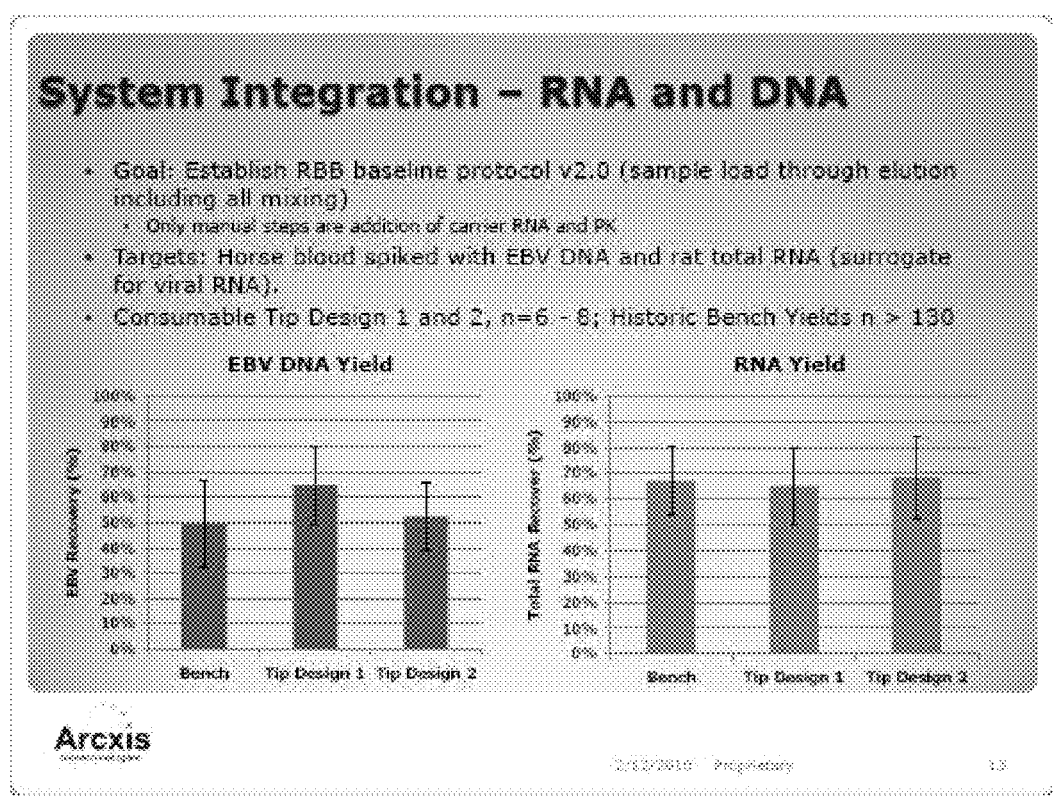
FIG. 17 illustrates sample results obtained by the claimed invention when assaying samples for DNA and RNA content.
Figure 18:
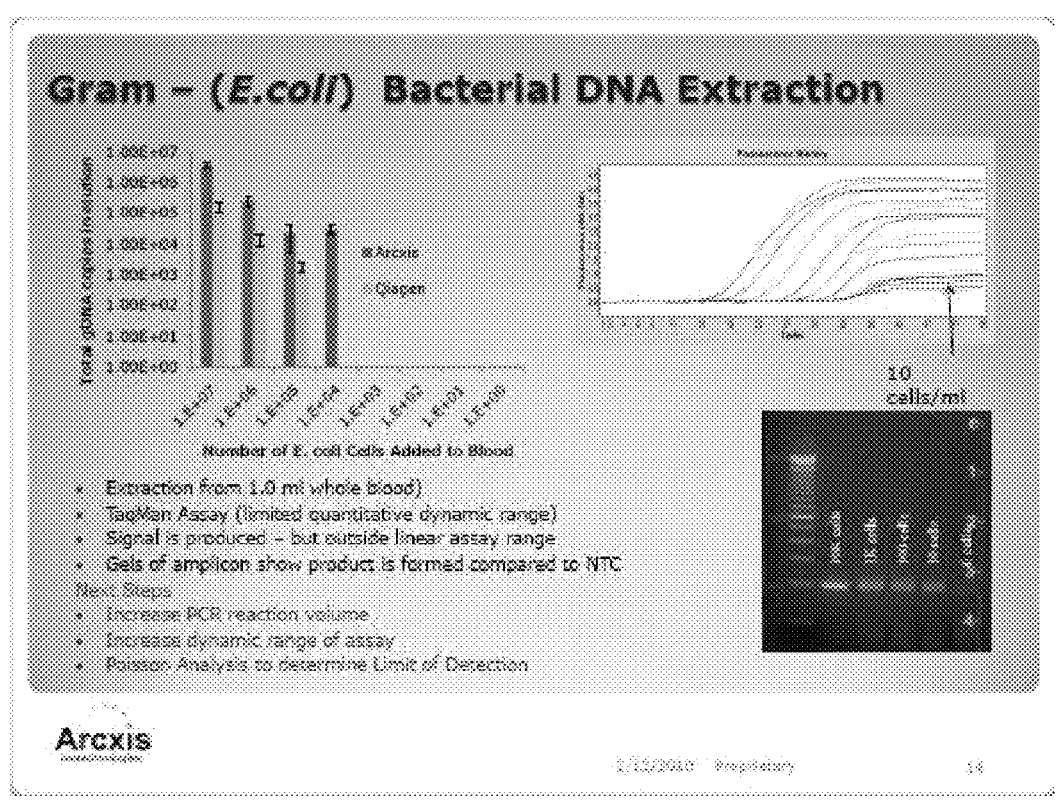
FIG. 18 illustrates sample results achieved by the claimed invention when extracting DNA from *E. coli* bacteria.
Figure 19:
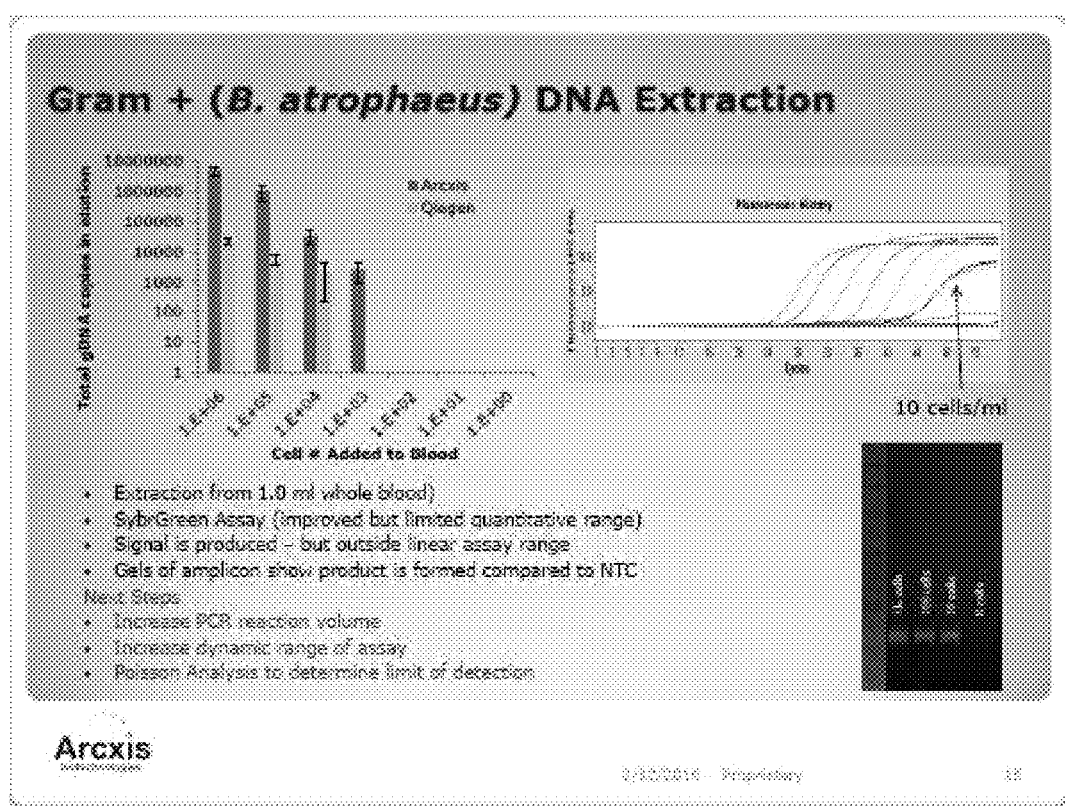
FIG. 19 illustrates sample results achieved by the claimed invention when extracting DNA from *B. atrophaeus* bacteria.

FIG. 17 illustrates experimental results attained by the claimed invention. These assays were performed to assay for EBV DNA and RNA. FIG. 18 depicts the claimed invention's extraction of DNA from *E. coli* bacteria. FIG. 19 depicts the claimed invention's extraction of DNA from *B. atrophaeus*.

Figure 20:
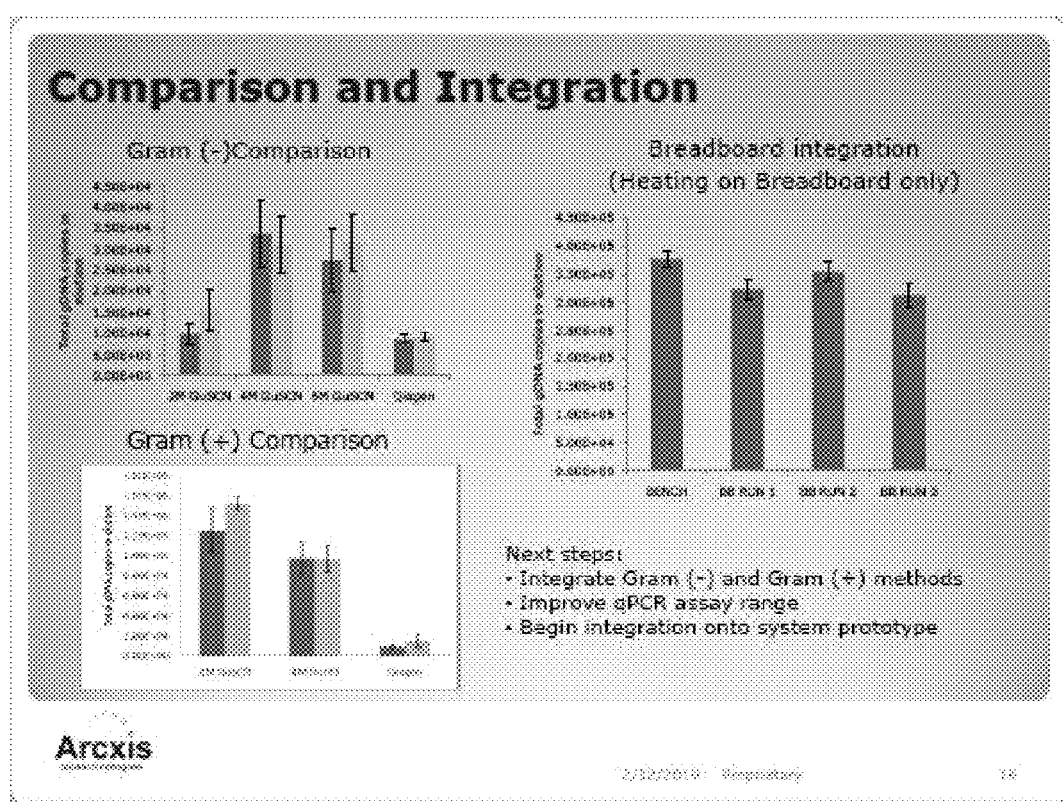
FIG. 20 compares the performance of the claimed invention against a Qiagen® product.
Figure 21:
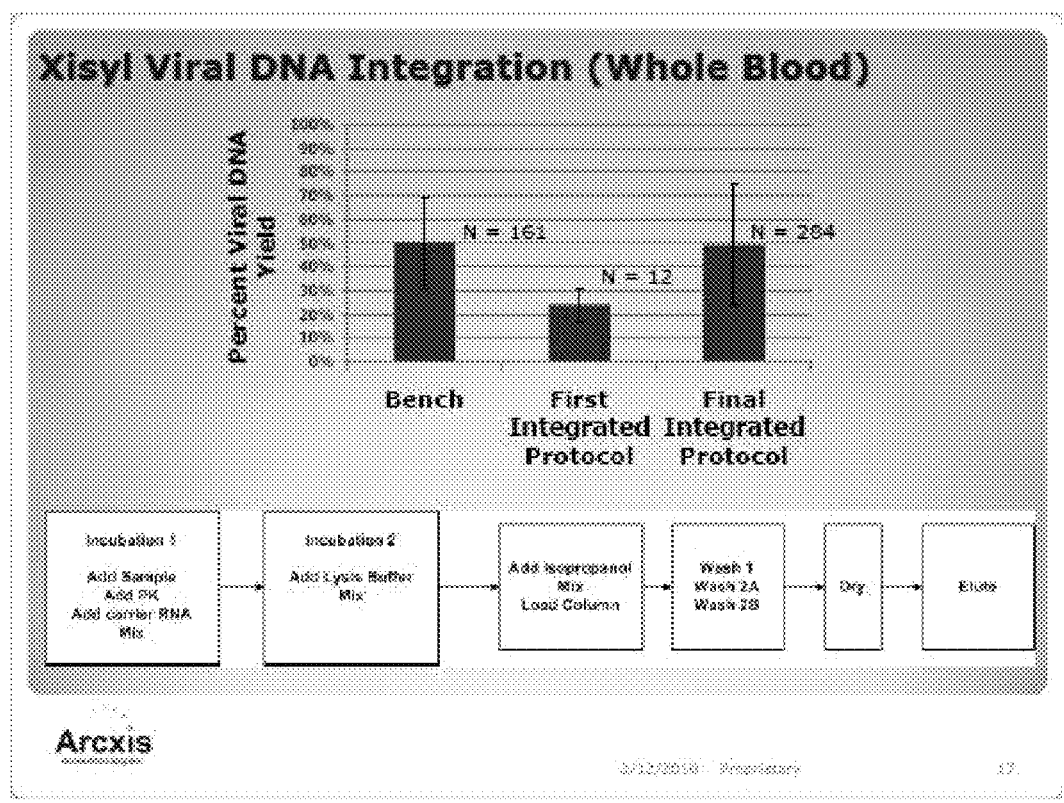
FIG. 21 illustrates the claimed invention's performance of viral DNA extraction.
Figure 22:
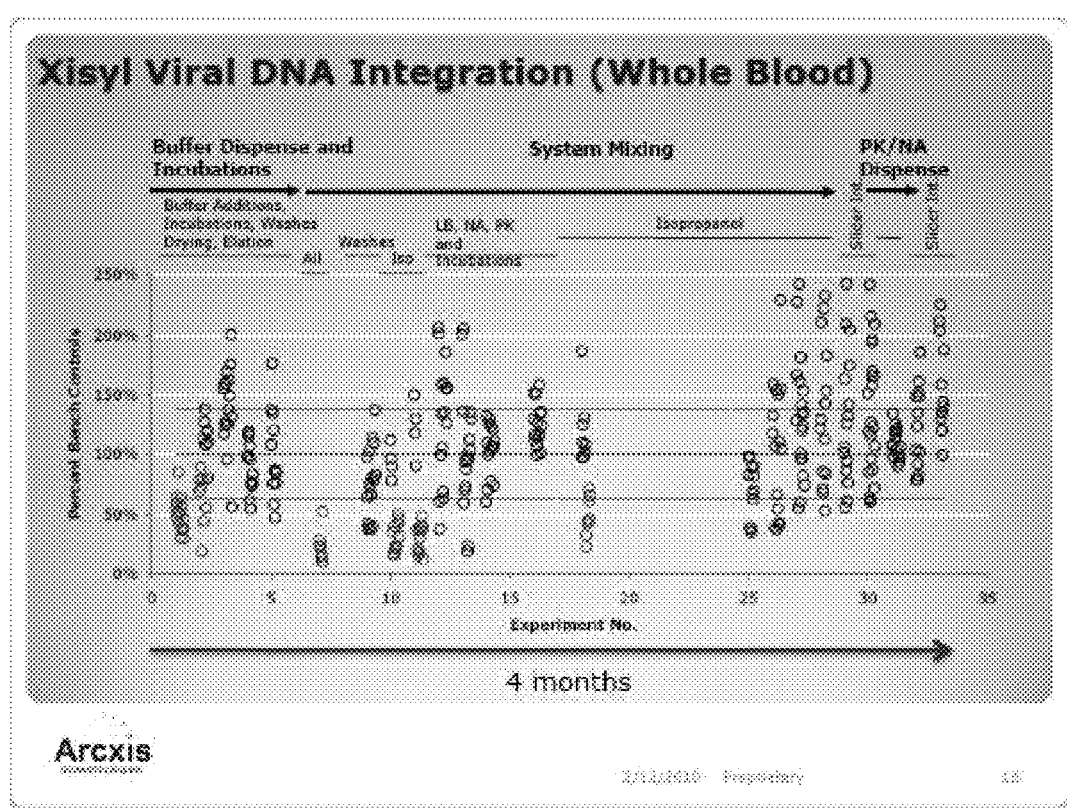
FIG. 22 illustrates the claimed invention's performance of viral DNA extraction.
Figure 23:
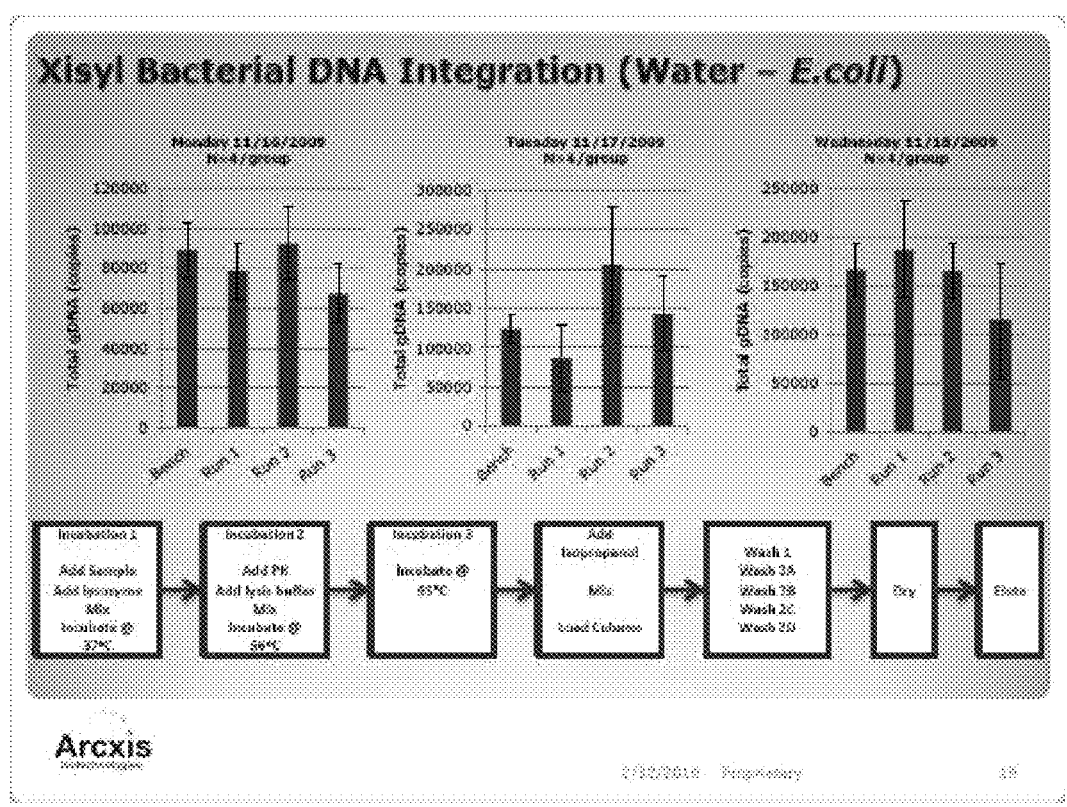
FIG. 23 illustrates the claimed invention's performance of bacterial DNA extraction.
Figure 24:
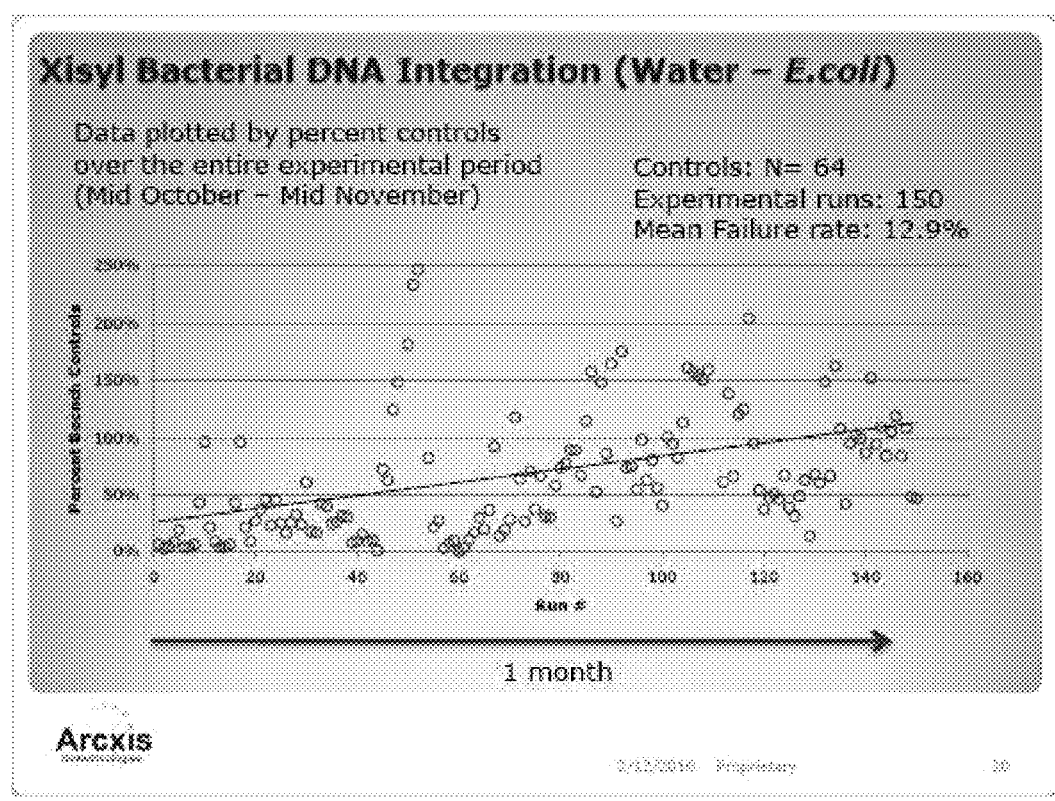
FIG. 24 illustrates the claimed invention's performance of bacterial DNA extraction.

FIG. 20 depicts a comparison between the claimed invention and a Qiagen® product. FIG. 21 illustrates experimental data generated by the claimed invention.

Figure 25:
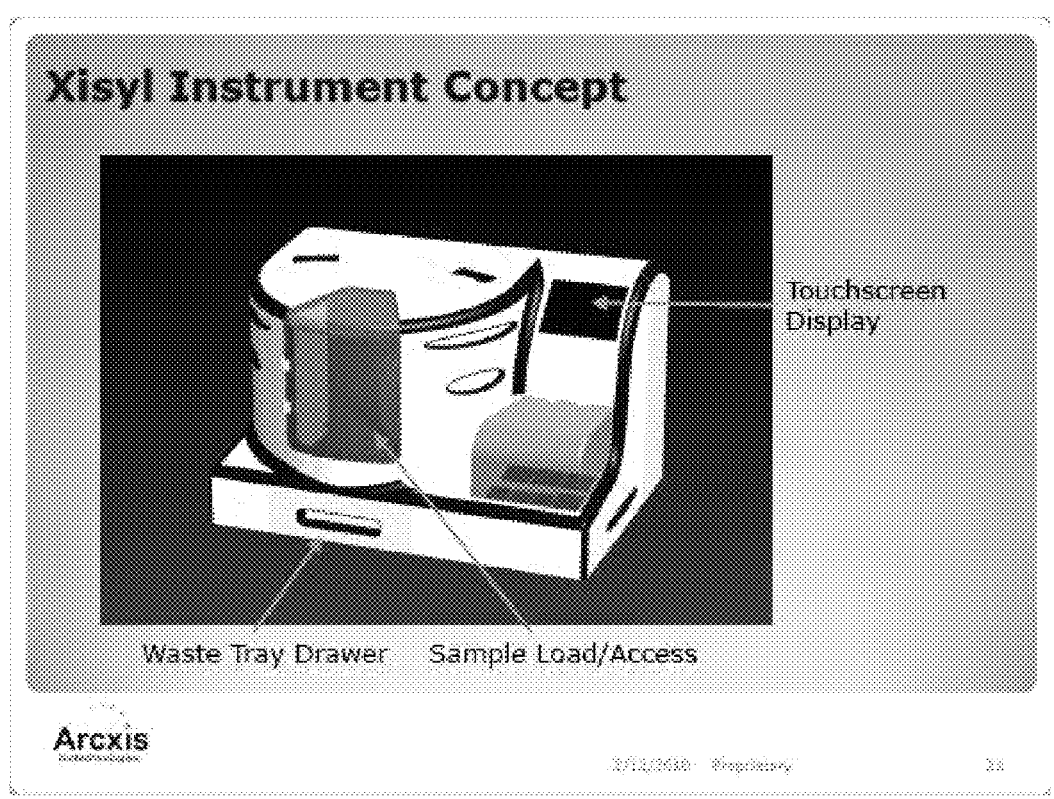
FIG. 25 is a non-limiting embodiment of the claimed invention.
Figure 26:
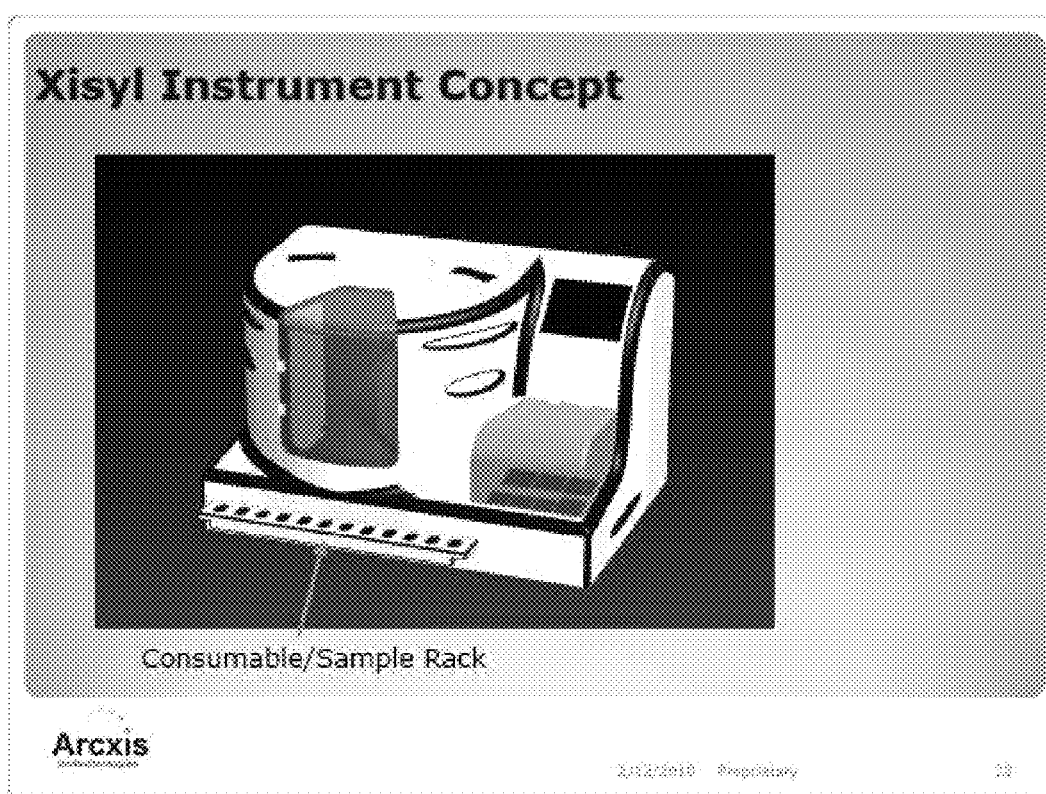
FIG. 26 is a non-limiting embodiment of the claimed invention.
Figure 27:
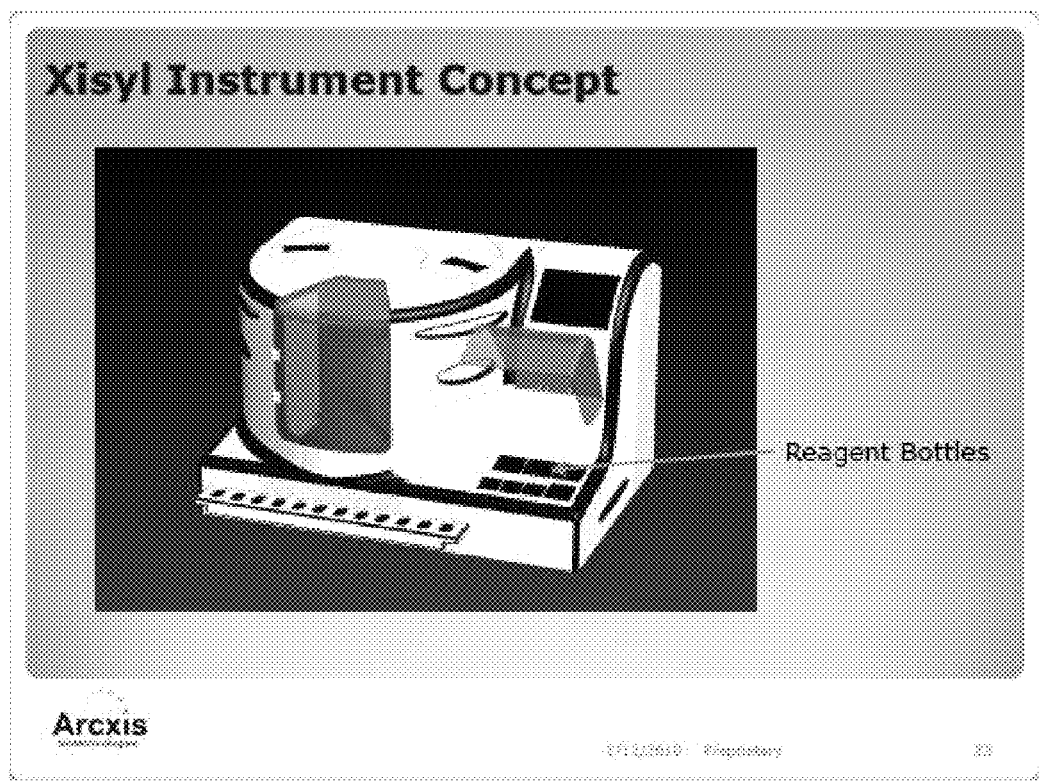
FIG. 27 is a non-limiting embodiment of the claimed invention.
Figure 28:
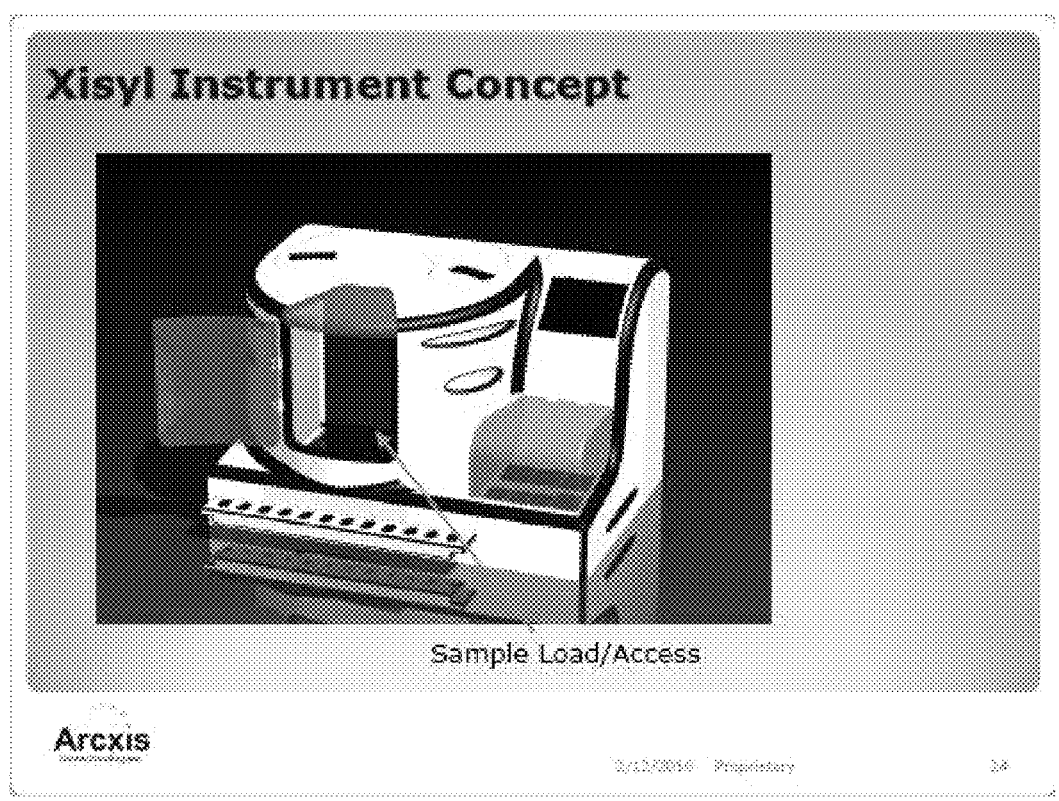
FIG. 28 is a non-limiting embodiment of the claimed invention.

FIG. 25 depicts a non-limiting embodiment of the claimed invention. As shown, samples or even purification cartridges may be introduced at the "sample load/access" site. A touchscreen controller enables user control of the device. A waste tray drawer may be used to store excess buffer or other material evolved during experimentation. FIG. 26 depicts a non-limiting embodiment having a consumable/sample rack. This rack may be used to hold samples or purification cartridges. In another embodiment, shown in FIG. 27, reagent bottles or pouches may be held on the system. FIG. 28 depicts a system having a sample loading door, which can be opened to allow for introduction of sample or even purification cartridges.

Figure 29:
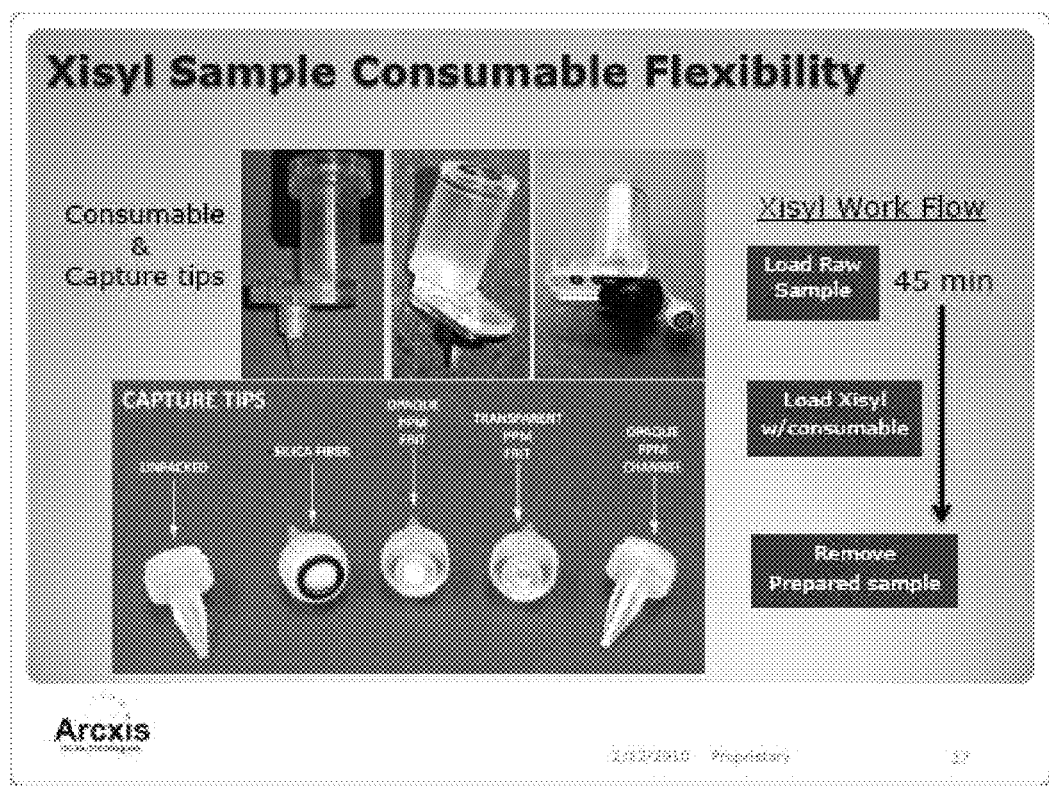
FIG. 29 illustrates various configurations for molecular capture regions according to the claimed invention.

Additional consumables are shown in FIG. 29. The top three images in the figure show sample consumables (i.e., purification cartridges). The left hand image shows a reaction chamber mounted on a cartridge body. The middle image shows the reaction chamber mounted on the cartridge, and the right-hand image shows a sliding receiver for the capture chamber mounted on a cartridge so as to have the ability to slide between a first position (in fluid communication with the reaction chamber) and a second chamber (in fluid communication with a fluid inlet). The bottom images of the figure show various capture chambers and capture materials; as shown, the conical elution tips can accommodate a number of different materials having a number of different form factors.

Figure 30:
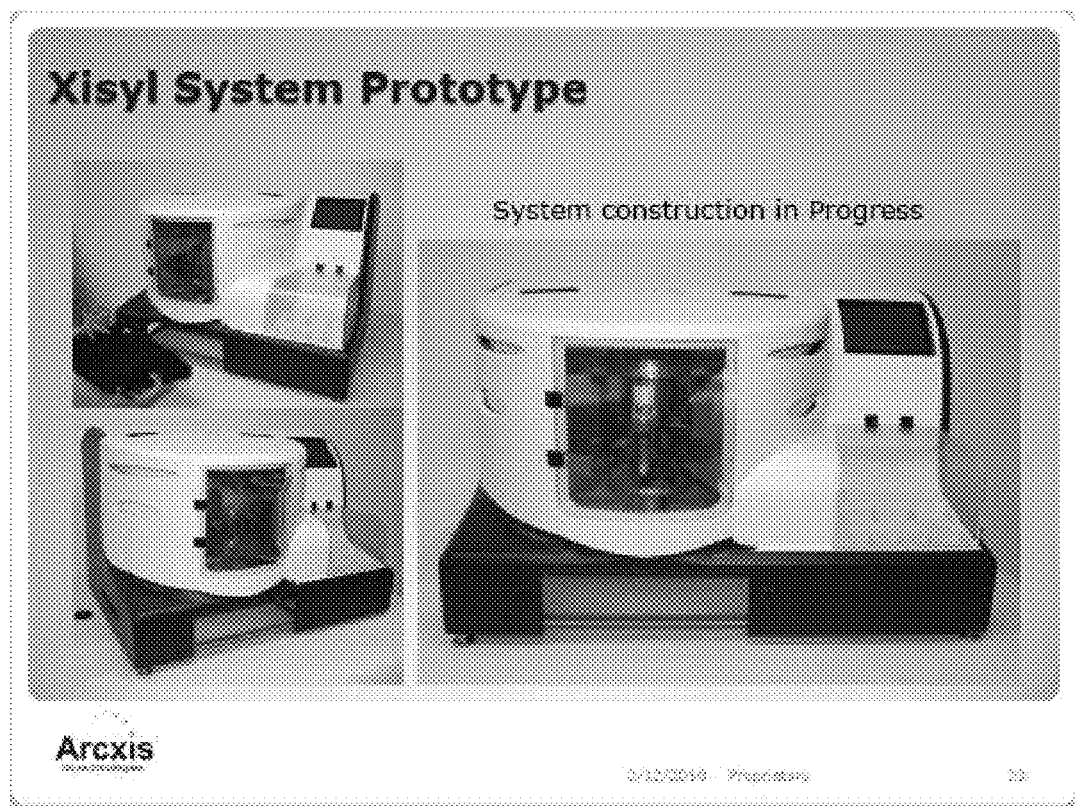
FIG. 30 illustrates non-limiting embodiments of the claimed invention.

An exemplary system is shown in FIG. 30, which figure illustrates a system having a sample loading door.

Figure 31:
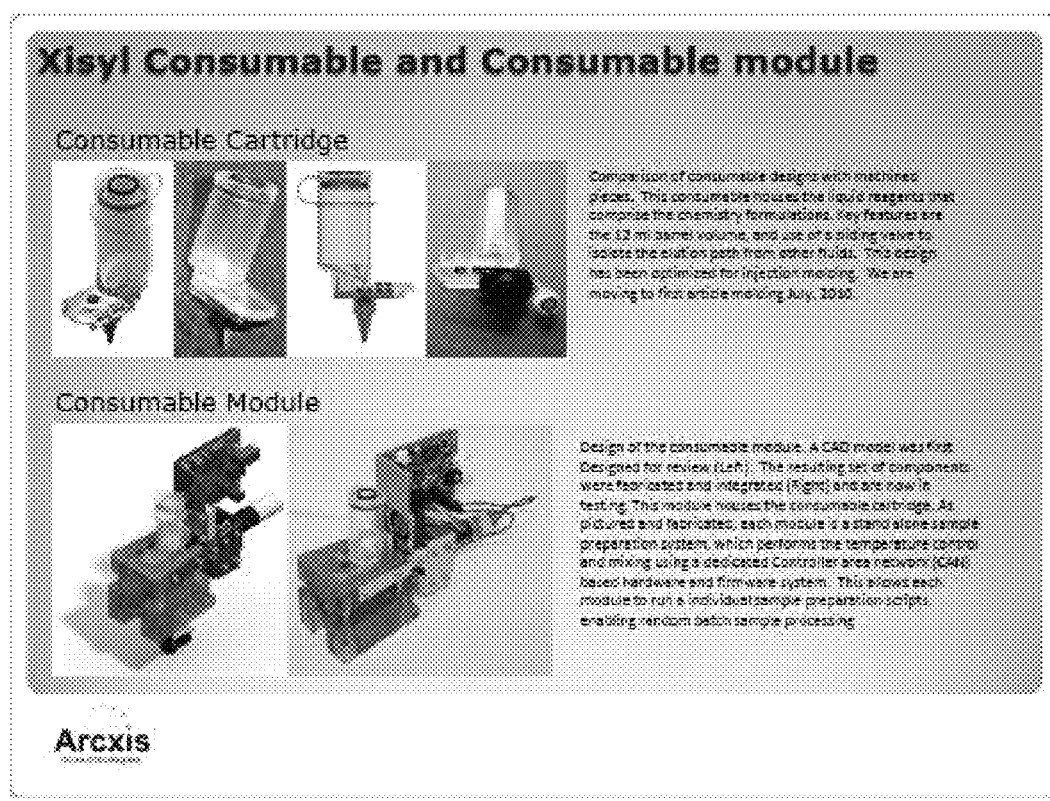
FIG. 31 illustrates non-limiting embodiments of purification cartridges and receiving mounts.

FIG. 31 provides additional images of the consumable cartridge (upper image) and a module that interacts with the cartridge. As shown in the lower image, the cartridge mates with the module, where the module introduces fluids and applies (or removes) heat as necessary for operation of the device. In some embodiments, the module includes a pressure source configured to deliver pressure to various fluid elements (chambers, valves, and the like) of the cartridge.

Additional Discussion

Provided herein are, inter alia, automated instruments and consumables that enable easy, robust, sample preparation of nucleic acids. To enable automated extraction of nucleic acids, methods for the purification from viral RNA and DNA from plasma and whole blood are disclosed, along with methods for extracting gram positive and gram positive bacterial genomic DNA. Extracted nucleic acids are detected by, e.g., using real time PCR.

These methods are integrated on an automated or semi-automated platform, and the results demonstrated that the disclosed methods efficiently extract nucleic acids as compared to conventional the bench top processes. To determine the extraction efficiency of automated systems, purified DNA or RNA of known concentrations was spiked into horse whole blood, and the extraction of nucleic acids from plasma and whole blood was fully automated.

The present invention provides devices and methods that integrate all steps for lysis of viral, bacterial and eukaryotic cells as well as the extraction and purification of the target analytes. The disclosed devices enable the user to load the sample into a cartridge and place that cartridge on the instrument to enable automated sample preparation. A module effects the addition of enzymes, buffers, washing and elution reagents, as well as performs multiple temperature controlled incubation and mixing steps to ensure efficient sample capture and purification. In one suitable embodiment, the systems accommodate twelve of the consumable modules that may operate independently from one another, enabling random batch method execution. This allows the user to process several different sample types with a variety of methods during a single run. The systems are scalable and can be adapted to accommodate additional samples. In some embodiments, multiple systems are connected to one another so as to allow large-scale processing of larger numbers of samples.

Consumable Design and Operation:

To enable completely automated sample preparation a consumable—known as a purification cartridge—allows all sample preparation steps to be conducted in a single cartridge (FIGS. 1, 5, 14).

In the field of molecular diagnostics, typically larger sample sizes—rather than smaller samples—are needed to attain the necessary assay sensitivity. Accordingly, in some embodiments, the cartridge is capable of processing samples as large as 1 ml, 2 ml, or even 5 ml of raw sample input.

For some methods that utilize chaotropic salts and alcohol based precipitation methods, the processing vessel is about ten (10) times the volume of the original sample size.

For effective lysis, a device suitably has the ability to effectively mix the sample with a variety of enzymes, buffers and solvents being added to the sample. To enable this mixing, some embodiments of the present invention make use of a magnetic disk that serves the function of sealing the cartridge during sample loading and transport of the consumable to the instrument. This sample containment is useful when processing samples that contain potentially hazardous pathogenic agents. To accomplish this, the disk may be press-fit inserted into the cartridge cap to prevent liquid flow out of the top of the consumable during filling and transport to the instrument (FIGS. 1, 5, 14). Once loaded onto an instrument or cartridge mount, the disk may be ejected from the sample cap into the sample fluid. Depending on the extraction method, a buffers are sequentially injected into the consumable cartridge, and during these filling steps, magnets located proximate to the disk may be rotated to enable non-contact mixing of the enzymes, buffer and alcohols within the consumable cartridge. This reduces or eliminates the possibility of sample to sample carryover cross contamination.

Extraction and purification of the target analytes is performed using a capture material located at the base of the consumable cartridge. This capture material is suitably contained within a movable capture chamber which may be slidably mounted on the consumable base via a rail system that enables the capture material to be positioned at one of two positions, or more positions in embodiments not shown. In the first position, the capture material is positioned so that the reaction chamber (where the lysis takes place) is sealed, and remains in this position while preparation steps prior to the capture step are conducted.

Following the lysing, the slidably-mounted capture material is actuated to move into a second position where target analyte extraction onto the capture material is conducted. During this extraction step the consumable module is positioned directly beneath an air input line that when contacted to the consumable enables pressurization of the cartridge by the instrument. This pressurization forces the prepared sample through the capture material enabling analyte extraction.

The systems may also include a vacuum line, which line suitably has little to no contact with the reaction chamber, and removes material exiting the elution tip or capture region. The tip of the cartridge is suitably configured such that the tip is sufficiently close to the vacuum line so as to minimize the accumulation of waste in the tip. In this way, the vacuum line may be used to keep the tip "clear" by drawing material out of the tip. Once extracted, several washes of the internal vessel of the consumable cartridge are conducted by alternating the dispensing of solutions with the pressurization of the consumable. When these washes are completed and the capture material has been dried, the slider is again moved into the first position directly underneath the elution port on the consumable base. This enables removal of any remaining contaminants that can and do affect the downstream molecular diagnostic analysis.

To elute a sample, the cartridge is first positioned below the reaction chamber. Here the cartridge is under temperature control, and the capture material can be blown dry. Once dry, the capture material is slidably moved to the elution path of the base and an elution buffer is loaded onto capture material to effect removal of the purified analytes residing on the capture material.

A useful feature of a sample preparation system or molecular diagnostic analysis platform is the ability to limit or eliminate sample cross contamination. The present invention addresses this challenge by performing non-contact filling and mixing by use of a module or mount that direct the internal workings of the cartridge.

For example, the loading of buffer and solvents is performed using a nozzle that is positioned to allow the solutions to be added to the consumable cartridge without contacting the sample itself. To enable rotation of a magnetic disk disposed within the cartridge (described elsewhere herein), a rare earth magnet is suitably located at the base of the cartridge. Such magnets can be moved or rotated at variable speeds for a duration consistent with the processing steps being applied to an individual consumable module. Another advantage besides reducing sample contamination is the reduction of consumable pieces. Other, existing systems utilize a pipette technique to aspirate and dispense buffers, and also achieve mixing, but such systems greatly increases the use of consumable tips, and the same air path is used for multiple locations providing a chance of cross contamination.

In some embodiments, individual modules are operated independently using a controller—area network (CAN) communication system. This system enables each consumable module to operate on an individual script or an individual set of process steps during a single sample preparation run. Each module may contain a discrete electronics hardware and software package that is in electronic communication with a central controller or other device. This electronic package enables the central controller or motherboard to execute high level commands communicated to the slaved consumable module that can effect control (e.g., PID control) of the temperature, mixing and positioning of the cartridge and its components. In this way the motherboard contains all of the high level commends for the various methods that can be operated in tandem.

In one non-limiting embodiment, the consumable module possesses three main functionalities that are controlled by the module electronic board. The first of these functions is magnetic mixing, which is suitably conducted using a motor driven rotational motion that, when actuated, effects rotation of the magnetic disk within the fluid containing vessel. Various disk materials can be used; nickel-plated magnetic disks were found to be suitable, as were Teflon™-coated magnetic disks.

A second operation of the consumable module is the temperature control of the consumable. Fully automated sample preparation may entail use of multiple enzymes that have optimal proteolytic or nucleolytic activity at temperatures above 25° C.

To perform the incubation with the consumable cartridge, an aluminum sleeve may be used to transfer and extract heat from the consumable module. The sleeve may be heated using a thermoelectric cooler or resistive heater under PID control to raise and maintain the internal temperature of the consumable cartridge.

The system is also suitably capable of removing heat from the consumable. After the heated incubations are complete, a fan located on the back of the thermoelectric cooler may be used to effect convection-based heat removal from the consumable module and the consumable cartridge. The system may also utilize a thermoelectric cooler to achieve heat removal.

One non-limiting example is the protocol for gram positive bacterial DNA extraction from whole blood. This method suitably includes three incubation steps for the preparation of the sample for extraction.

The first incubation, using lysozyme, uses an incubation at about 37° C. for a period of 5-45 minutes depending on the bacterial species. For the second incubation using proteinase K, the optimal incubation temperature is 56° C., with a duration of at least about 15 minutes. A final incubation step is required to denature the genomic DNA at 95° C. to increase the efficiency of the extraction. Due to the length of these incubations, cooling of these samples prior to extraction is suitable, and the present systems cooled the samples to room temperature within a time frame of 3-5 minutes after this 95° C. step.

The third operation of the consumable system is the positioning of the capture tip between the elution port and the sample capture port. The positioning of this tip is controlled by a gear driven DC motor 24 that actuates an aluminum plate that resides beneath the consumable cartridge. At the base of the slider subcomponent, the capture tip extends into a hole within this plate. At various times during the sample preparation procedure this gear driven plate is actuated between the capture and elution positions. In this way the sample preparation, alcohols, and wash buffer components are physically separated from the elution tip.

The disclosed devices are suitably constructed so as to separate their major electrical components and fluidic components. As shown in, e.g., FIG. 10, the system was designed to compartmentalize the pumps, mother board, and touch screen on the right side of instrument, while the consumable modules, waste and elution manifolds are located on the left compartment of the instrument. This was designed as a safety measure in the unlikely event there is a failure to contain the fluids in any of the major liquid handling components.

The current system was designed to accommodate twelve consumable modules on a rotary platen. In this format, the consumable cartridges can be positioned at various dispensing and air flow ports to enable automated preparation of any number of samples up to the full complement of consumable modules. As described, each module has the ability to operate independently of one another to enable separate control and random batch or random access sample preparation. In some embodiments, a module may include a power connection along with a connection (e.g., a CAN connection) for receiving data, transmitting data, or both. The modules are also suitably connected to a waste manifold at the base of the instrument. This manifold evacuates waste from the capture tip under vacuum, without actually contacting the capture tip, which prevents contaminants such as chaotropic buffers and alcohol from accumulating on the external surface of the capture tip. Note that if such contaminants are present, they can inhibit the downstream molecular diagnostic analysis.

During the extraction of the samples, the capture region interfaces with this manifold to remove the chaotropic buffers and alcohols to a waste container. The waste container is suitably connected to the waste manifold using a quick connect system that enables the user to remove waste materials.

The designed system has the ability to completely automate the process of sample preparation from a variety of sample types. To perform this sample preparation process the user places the consumable in a rack that is contains multiple cartridges. The samples typically are loaded within a biosafety cabinet. Once loaded, the consumable cartridges are transported to the instrument for loading on the consumable module within the instrument. The user first actuates the touch screen and selects the intended method desired. The consumable device can then be presented to a bar code scanner which verifies the method selected and the loading position. The touch screen then indicates the system is ready for loading. The user then opens the front access door, and inserts the consumable cartridge into the consumable module which is a "snap" fit. In a similar fashion each consumable is loaded, and when complete, the user again uses the touch screen to start the preparation run.

Once the sample preparation run is actuated, the system ejects the magnetic disks from the cartridge cap into the fluid sample. Appropriate buffers are added to the cartridge and the samples are mixed using the magnetic disk apparatus. Depending on the methods selected for each given consumable module, various enzymes or other reagents are dispensed into the appropriate cartridge or cartridges. The consumable cartridges are, if necessary, heated to the appropriate temperatures to allow optimal activity. During these incubation steps the contents of the cartridge are suitably mixed. Several of the methods employ multiple enzymatic steps which require multiple temperatures as described above. In some embodiments, when these incubations are complete, additional buffers containing chaotropic salts are suitably dispensed into the consumable cartridge, although chaotropic buffers are not necessarily required. These steps are typically also followed by an incubation and mixing period, either or both of which may last for a few seconds or even for 5, 10, 20, or 30 minutes. ATA (from the Sigma company) is suitable for RNase inhibition. After the enzymatic and lysis buffer steps are completed, a suitable volume of alcohol is dispensed into the consumable cartridge. During this step, mixing can be implemented and is continued for a period between 1-10 minutes.

With the sample prepared for extraction, the slider-mounted capture chamber is suitably positioned by the system into the "load" position. Cartridges are then positioned beneath the "purge" port. The system raises the consumable module platen to compress the springs within the consumable modules and form air tight seals between the air port and the cap of the sample cartridge. With the seal pressure tight, the cartridge is pressurized to force the prepared sample through the capture material as described above. Sensors within the system architecture monitor the purge pressure during this operation, and when the sensors detect a significant pressure drop, a valve is suitably actuated to stop the pressurization of the cartridge. The system suitably includes a time out feature that will notify the user if a sample will not flow through the capture material, an important feature to preserve precious samples if there are not properly loaded.

Once loaded, wash buffers are dispensed into the consumable cartridge to remove unwanted contaminants remaining within the consumable cartridge and on the capture material. Depending on the method selected, the number of washes may vary, which may depend on the turbidity and protein load of the sample being prepared.

With the loading and purification of the sample completed, the system effects sample elution. In this step, a cartridge is suitably positioned (e.g., rotated on the platen) to the elution manifold. Once positioned beneath the elution manifold, the slider once again positions the capture material orifice beneath the elution port on the cartridge base. With the cartridge in the elution position, the system then compresses the consumable module against the elution manifold to form a pressure tight seal between the elution port of the cartridge and the ports located on the elution manifold. This may be performed before the module is actuated to the "elute" position. The elution fluid is expressed through the capture tip to elute the sample into a vessel (e.g., a micro centrifuge tube).

Example 1

Extraction of Viral DNA from Whole Blood and Plasma

In one non-limiting example, a consumable was used for the extraction of viral DNA in whole blood or plasma.

Approximately 40,000 copies of Epstein Barr viral DNA were spiked into a horse whole blood sample. The sample was then loaded into a consumable cartridge according to the claimed invention and was capped. The sample was placed on the instrument for processing.

The first step in this protocol was the additional of Proteinase K. The sample is incubated and mixed for ten minutes at room temperature. A volume of 2.0 ml of lysis buffer containing 4.9M GuSCN, 0.035M EDTA (pH 8.0), Triton X-100 (2.3%), 0.088M Tris-HCl was then added to the blood sample and incubated for 30 minutes at 56° C. Once this incubation is complete, 3.0 ml 80% isopropanol was added to the sample and mixed for a period of ten minutes.

Once the mixing was complete, the system effected a purge to force the prepared sample through the capture matrix, in this case a Whatman (Piscataway, N.J.) silica fiber matrix to extract viral DNA. Once extracted, several wash buffers were sequentially dispensed into the cartridge. Specifically, 2 volumes (0.5 ml) of Wash 1 containing 0.5M GuHCl, 0.002M EDTA (pH 8.0), 0.05M Tris-HCL in 80% ETOH followed by two volumes (0.5 ml) of Wash 2 containing 70% ethanol were sequentially dispensed into the consumable cartridge and each wash was subsequently purged from the consumable through the capture material prior to addition of the subsequent wash buffer.

Once removal of the unwanted contaminants was completed, the slider moved into position to enable elution of the sample. The capture material was purged with air at an elevated temperature, then elution buffer, Tris-EDT or sterile water, was dispensed to the capture material to allow sample elution into the microcentrifuge tube. The contents of this tube were analyzed using real-time PCR on an ABI 7500 Fast thermocycler using appropriate nucleic acid primers and a dual labeled probe for detection of the amplified DNA.

Example 2

Extraction of RNA from Whole Blood and Plasma

In another example, a consumable was used for the extraction of viral RNA in whole blood or plasma. Multiple copies of rat total RNA were spiked into a horse whole blood sample, and the sample was loaded into the consumable cartridge and capped. The sample was placed on the instrument for processing.

The first step in this protocol was addition of Proteinase K. The sample was incubated and mixed for ten minutes at room temperature. A volume of 2.0 ml of lysis buffer containing 4.9M GuSCN, 0.035M EDTA (pH 8.0), Triton X-100 (2.3%), 0.088M Tris-HCl was then added to sample and incubated for 30 minutes at 56° C. Once this incubation was complete, 3.0 ml of 80% isopropanol was added to the sample and mixed for a period of ten minutes. Once the mixing was complete, the system enabled the purge function to force the prepared sample through the capture matrix, in this case a Whatman (Piscataway, N.J.) silica fiber matrix, to extract the viral RNA Once extracted, several wash buffers were sequentially dispensed into the cartridge. Specifically 2 volumes (0.5 ml) of Wash 1 containing 0.5M GuHCl, 0.002M EDTA (pH 8.0), 0.05M Tris-HCL in 80% ETOH followed by two volumes (0.5 ml) of Wash 2 containing 70% ethanol were sequentially dispensed into the consumable cartridge and each wash was subsequently purged from the consumable through the capture material prior to addition of the subsequent wash buffer. Once removal of the unwanted contaminants was completed, the slider was moved into position to enable elution of the sample.

The capture material was purged with air at an elevated temperature, then the elution buffer, DEPC treated water, was dispensed through the capture material to allow sample elution into the microcentrifuge tube. The contents of this tube was analyzed using real-time PCR on an ABI 7500 Fast thermocycler. The efficiency of RNA extraction was quantitated using a commercial pre-designed primer and probe set (rat-Gusb) from Applied Biosystems (Foster City, Calif.). Each reaction contained 1.0 µl of sample which was added to 9.0 µl of PCR master mix containing 5 µl of 2×Taqman fast universal master mix, 0.100 µl 20 U/µL Rnase inhibitor, 0.125 µL of 50 U/µL MultiScribe reverse transcriptase, 0.5 µl of 20×Gusb primer/probe mix with FAM, and 3.275 µl DEPC treated water for a final volume of 10 µl for amplification on an 7500 Fast real time PCR machine (ABI, Foster City, Calif.). The included a 30 min reverse transcriptase step at 48° C., a 20 s activation step at 95° C. followed by 40 cycles of 95° C. for 3 s and 60° C. for 30 s.

Example 3

Extraction of Total RNA from Tissues

In another exemplary embodiment, a consumable was used for the extraction of total RNA from tissue homogenates containing 5-500 mg of rat tissue. Tissue was placed into 1.0 ml of RNA stabilization buffer such as a high salt buffer (or RNAlater, Ambion/Life Technologies, Carlsbad Calif.) and homogenized.

The homogenized materials were directly deposited in the consumable cartridge and capped. The sample was placed on the instrument for processing.

The first step in this protocol was the addition of Proteinase K and the associated buffer. The sample was incubated and mixed for ten minutes at room temperature. A volume of 2.0 ml of lysis buffer containing 4.9M GuSCN, 0.035M EDTA (pH 8.0), Triton X-100 (2.3%), 0.088M Tris-HCl was then added to the sample and incubated for 30 minutes at 56° C. Once this incubation was complete, 3.0 ml or 80% isopropanol was added to the sample and mixed for a period of ten minutes. Once the mixing was complete the system enabled the purge function to force the prepared sample through the capture matrix, in this case a Whatman (Piscataway, N.J.) silica fiber matrix to extract the RNA. Once extracted, several wash buffers were sequentially dispensed into the cartridge. Specifically 2 volumes (0.5 ml) of Wash 1 containing 0.5M GuHCl, 0.002M EDTA (pH 8.0), 0.05M Tris-HCL in 80% ETOH followed by two volumes (0.5 ml) of Wash 2 containing 70% ethanol were sequentially dispensed into the consumable cartridge and each wash was subsequently purged from the consumable through the capture material prior to the addition of the subsequent wash buffer. Once removal of the unwanted contaminants was complete, the slider was moved into position to enable elution of the sample. The capture material was purged with air at an elevated temperature, then the elution buffer, DEPC treated water, was dispensed through the capture material to allow sample elution into the microcentrifuge tube. The contents of this tube was analyzed using real-time PCR on an ABI 7500 Fast thermocycler. The efficiency of RNA extraction was quantitated using a commercial pre-designed primer and probe set (rat-Gusb) from Applied Biosystems (Foster City, Calif.). Each reaction contained 1.0 µl of sample which was added to 9.0 µl of PCR master mix containing 5 µl of 2×Taqman fast universal master mix, 0.100 µl 20 U/µL Rnase inhibitor, 0.125 µL of 50 U/µL MultiScribe reverse transcriptase, 0.5 µl of 20×Gusb primer/probe mix with FAM, and 3.275 µl DEPC treated water for a final volume of 10 µl. The protocol for amplification on an 7500 Fast real time PCR machine (ABI, Foster City, Calif.) included a 30 min reverse transcriptase step at 48° C., a 20 s activation step at 95° C. followed by 40 cycles of 95° C. for 3 s and 60° C. for 30 s. Standard curves for Gusb RNA were created from dilutions of rat liver total RNA. Extraction efficiency was calculated by quantifying Gusb presence on the total RNA standard curves; the extraction efficiency of rat total RNA from whole blood was approximately equivalent to bench top sample preparation.

Example 4

Extraction of mRNA from Cryopreserved Hepatocytes

In one example of the system operation of the sample preparation platform a consumable was used for the extraction of mRNA from isolated cells. mRNA was isolated from cell suspensions of cultures containing $1\times10^2$-$1\times10^8$ cells. The cells were dispensed into the consumable cartridge and capped. The sample was placed on the instrument for processing. The first step in this protocol was the additional of Proteinase K. The sample was incubated and mixed for ten minutes at room temperature. A volume of 2.0 ml of lysis buffer containing Aurintricarboxylic acid (ATA) (3M), TMAC (2M), Triton X-100, (0.035%), pH (7.4), was added to the cell containing cartridge and mixed for approximately 10 minutes. Once mixing was complete the system enabled the purge function to force the prepared sample through the capture matrix, which is composed of a porous polymer monolith functionalized with a dT oligmer of approximately 30-100 bases in length.

Once the capture was complete, the capture material was then washed with a series of buffers. The first of these wash steps contained a buffer that consists of TMAC (2M), Triton X-100, (0.035%), pH (7.4). In the second wash step, the captured sample was washed with TMAC (0.1M), Triton X-100 (0.125%), pH (7.4). The washed sample was then air-dried to remove wash buffers before the elution of the sample. When these steps were concluded, the capture tip of the consumable cartridge was warmed to 75° C., and the sample was eluted into an external collection vial using DEPC treated water.

Example 5

Extraction of mRNA from Tissues

In another non-limiting example, a consumable was used for the extraction of mRNA from tissue homogenates containing 5-500 mg of rat tissue. Tissues were placed into 1.0 ml of a RNA stabilization buffer such as a high salt buffer (or RNAlater, Ambion/Life Technologies, Carsbad Calif.) and homogenized. The homogenized samples were then dispensed into the consumable cartridge and capped. The sample was placed on the instrument for processing. The first step in this protocol was the additional of Proteinase K.

The sample was incubated and mixed for ten minutes at room temperature. A volume of 2.0 ml of lysis buffer containing Aurintricarboxylic acid (ATA) (3M), TMAC (2M), Triton X-100, (0.035%), pH (7.4), was added to the tissue homogenate containing cartridge and mixed for approximately 10 minutes. Once the mixing was complete, the system enabled the purge function to force the prepared sample through the capture matrix, which is composed of a porous polymer monolith functionalized with a dT oligmer of approximately 30-100 bases in length. Once the capture was complete, the capture material was then washed with a series of buffers. The first of these wash steps contained a buffer that consists of TMAC (2M), Triton X-100, (0.035%), pH (7.4). In the second wash step the captured sample was washed with TMAC (0.1M), Triton X-100 (0.125%), pH (7.4). The washed sample was then air dried to remove all traces of wash buffers before the elution of the sample. When these steps were concluded, the capture tip of the consumable cartridge was warmed to 75° C., and the sample was eluted into an external collection vial using DEPC treated water.

Example 6

Sequence Selective Target Extraction from Whole Blood and Plasma

In another non-limiting example of the claimed invention, a consumable was used for the extraction of sequence selective target from whole blood or plasma.

Sequence selective extraction of target nucleic acids was accomplished using porous polymer monolith materials. A sample containing a specific analyte was dispensed into the consumable cartridge and capped. The sample was placed on the instrument for processing. The first step in this protocol was the additional of Proteinase K. The sample was incubated and mixed for ten minutes at room temperature. A volume of 2.0 ml of lysis buffer containing Aurintricarboxylic acid (ATA) (3M), TMAC (2M), Triton X-100, (0.035%), pH (7.4), was added to the cell containing cartridge and mixed for approximately 10 minutes. Once the mixing was complete, the system enabled the purge function to force the prepared sample through the capture matrix, which is composed of a porous polymer monolith functionalized with a sequence specific oligmer of approximately 30-100 bases in length. Once the sample capture was complete the capture material was then washed with a series of buffers. The first of these wash steps contains a buffer that consists of TMAC (2M), Triton X-100, (0.035%), pH (7.4). In the second wash step the captured sample was washed with TMAC (0.1M), Triton X-100 (0.125%), pH (7.4). The washed sample was then air dried to remove all traces of wash buffers before the elution of the sample. When these steps were concluded, the capture tip of the consumable cartridge was warmed to 95° C., and the sample was eluted into an external collection vial using either a Tris-EDTA buffer or pure water.

Example 7

Extraction of RNA and DNA from Formalin-Fixed Paraffin-Embedded (FFPE) Samples In another non-limiting example, a consumable was used for the extraction of RNA and DNA from FFPE tissue samples. Sections of a paraffin block were trimmed to reduce the amount of paraffin in the sample preparation. Blocks were then sectioned at a thickness of approximately 10-20 microns.

The sections were then deposited into a tube with 100% xylene to deparaffinize the tissue section. The tube is then centrifuged to pellet the deparaffinized samples. Xylene was removed by aspiration.

A second solution of 95% ethanol was added to the sample, mixed, centrifuged, and the ethanol is removed by aspiration. The sample was then reconstituted in water and added to the consumable cartridge for further preparation and analyte extraction. The deparafinized sample was placed on the instrument for processing.

The first step in this protocol was the addition of Proteinase K and the associated buffer. The sample was incubated and mixed for ten minutes at room temperature. A volume of 2.0 ml of lysis buffer containing 4.9M GuSCN, 0.035M EDTA (pH 8.0), Triton X-100 (2.3%), 0.088M Tris-HCl was then added to the sample and incubated for 30 minutes at 56° C. Once this incubation was complete, 3.0 ml or 80% isopropanol was added to the sample and mixed for a period of ten minutes. Once the mixing was complete, the system enabled the purge function to force the prepared sample through the capture matrix, in this case a Whatman (Piscataway, N.J.) silica fiber matrix to extract the RNA and DNA.

Once extracted, several wash buffers were sequentially dispensed into the cartridge. Specifically 2 volumes (0.5 ml) of Wash 1 containing 0.5M GuHCl, 0.002M EDTA (pH 8.0), 0.05M Tris-HCL in 80% ETOH followed by two volumes (0.5 ml) of Wash 2 containing 70% ethanol were sequentially dispensed into the consumable cartridge and each wash was subsequently purged from the consumable through the capture material. Once removal of the unwanted contaminants was complete the slider moved into position to enable elution of the sample. The capture material was purged with air at an elevated temperature, then the elution buffer, DEPC treated water, was dispensed to the capture material to allow sample elution into the microcentrifuge tube.

Example 8

Genomic DNA from Cells

In a non-limiting example, a consumable is used for isolation of genomic DNA from cell suspensions. Cell cultures containing $1\times10^2$-$1\times10^8$ cells were dispensed into the consumable cartridge and capped.

The first step in this protocol was the addition of Proteinase K and the associated buffer. The sample was incubated and mixed for ten minutes at room temperature. A volume of 2.0 ml of lysis buffer containing 4.9M GuSCN, 0.035M EDTA (pH 8.0), Triton X-100 (2.3%), 0.088M Tris-HCl was then added to sample and incubated for 30 minutes at 56° C. Once this incubation was complete, 3.0 ml of 80% isopropanol was added to the sample and mixed for a period of ten minutes. Once the mixing was complete the system enabled the purge function to force the prepared sample through the capture matrix, in this case a Whatman (Piscataway, N.J.) silica fiber matrix to extract the genomic DNA. Once extracted, several wash buffers were sequentially dispensed into the cartridge. Specifically 2 volumes (0.5 ml) of Wash 1 containing 0.5M GuHCl, 0.002M EDTA (pH 8.0), 0.05M Tris-HCL in 80% ETOH followed by two volumes (0.5 ml) of Wash 2 containing 70% ethanol were sequentially dispensed into the consumable cartridge and each wash was subsequently purged from the consumable through the capture material.

Once removal of the unwanted contaminants was complete, the slider was moved into position to enable elution of the sample. The capture material was purged with air at an elevated temperature, then the elution buffer, Tris-EDTA buffer or pure water, was then dispensed to the capture material to allow sample elution into the microcentrifuge tube.

Example 9

Extraction of Genomic DNA from Tissues

In a non-limiting example, a consumable was used for the extraction of DNA from tissue homogenates containing 5-500 mg of rat tissue. Tissues were placed into 1.0 ml of a suitable homogenization buffer to enable liberation of intracellular components, including nucleic acids. Lysate materials were then deposited into the consumable cartridge and capped. The sample was placed on the instrument for processing.

The first step in this protocol was the addition of Proteinase K and the associated buffer. The sample was incubated and mixed for ten minutes at room temperature. A volume of 2.0 ml of lysis buffer containing 4.9M GuSCN, 0.035M EDTA (pH 8.0), Triton X-100 (2.3%), 0.088M Tris-HCl was then added to sample and incubated for 30 minutes at 56° C. Once this incubation was complete, 3.0 ml of 80% isopropanol was added to the sample and mixed for a period of ten minutes. Once mixing was complete, the system enabled the purge function to force the prepared sample through the capture matrix, in this case a Whatman (Piscataway, N.J.) silica fiber matrix to extract the genomic DNA. Once extracted, several wash buffers were sequentially dispensed into the cartridge. Specifically 2 volumes (0.5 ml) of Wash 1 containing 0.5M GuHCl, 0.002M EDTA (pH 8.0), 0.05M Tris-HCL in 80% ETOH followed by two volumes (0.5 ml) of Wash 2 containing 70% ethanol were sequentially dispensed into the consumable cartridge and each wash was subsequently purged from the consumable through the capture material. Once removal of the unwanted contaminants was complete the slider was moved into position to enable elution of the sample. The capture material was purged with air at an elevated temperature, then the elution buffer, Tris-EDTA buffer or pure water, was dispensed to the capture material to allow sample elution into the microcentrifuge tube.

Example 10

Extraction of Bacterial DNA from Liquid Samples

In another example, a consumable was used for the extraction of bacterial DNA in variety of sample types including but not limited to whole blood and water samples.

Bacterial genomic DNA can be extracted from $10^1$-$10^8$ cells in either whole blood or water. To enable reproducible calculation of yield, a range of cell inputs, as calculated by absorbance or O.D., were spiked into either a horse whole blood or a tap water sample. The sample was then loaded into the consumable cartridge and capped. The sample was placed on the instrument for processing.

The first step in this protocol was the additional of lysozyme and a N-[tris(hydroxymethyl)methyl]-2-aminoethanesulfonic acid, 2-[(2-hydroxy-1,1-bis(hydroxymethyl)ethyl)amino]ethanesulfonic acid (TES) buffer. Samples were mixed briefly and allowed to incubate for approximately 5-60 minutes depending on the sample matrix. The second step in the extraction process was addition of Proteinase K. The sample was incubated and mixed for ten minutes at room temperature. A volume of 2.0 ml of lysis buffer containing 4.9M GuSCN, 0.035M EDTA (pH 8.0), Triton X-100 (2.3%), 0.088M Tris-HCl was then added to sample and incubated for 30 minutes at 56° C. A final incubation at 95° C. for 5-15 minutes was used to denature the bacterial genomic DNA. Once this incubation was complete, 3.0 ml of 80% isopropanol was added to the sample and mixed for a period of ten minutes. Once the mixing was complete, the system enabled the purge function to force the prepared sample through the capture matrix, in this case a Whatman (Piscataway, N.J.) silica fiber matrix to extract the bacterial DNA. Once extracted, several wash buffers were dispensed into the cartridge. Specifically 2 volumes (0.5 ml) of Wash 1 containing 0.5M GuHCl, 0.002M EDTA (pH 8.0), 0.05M Tris-HCL in 80% ETOH followed by two volumes (0.5 ml) of Wash 2 containing 70% ethanol were sequentially dispensed into the consumable cartridge and each wash was subsequently purged from the consumable through the capture material. Once removal of the unwanted contaminants was complete, the slider was moved into position to enable elution of the sample. The capture material was purged with air at an elevated temperature, then the elution buffer, Tris-EDTA buffer or pure water, was dispensed through the capture material to allow sample elution into the microcentrifuge tube.

Additional Disclosure

Consumable Design and Operation

Figure 33:
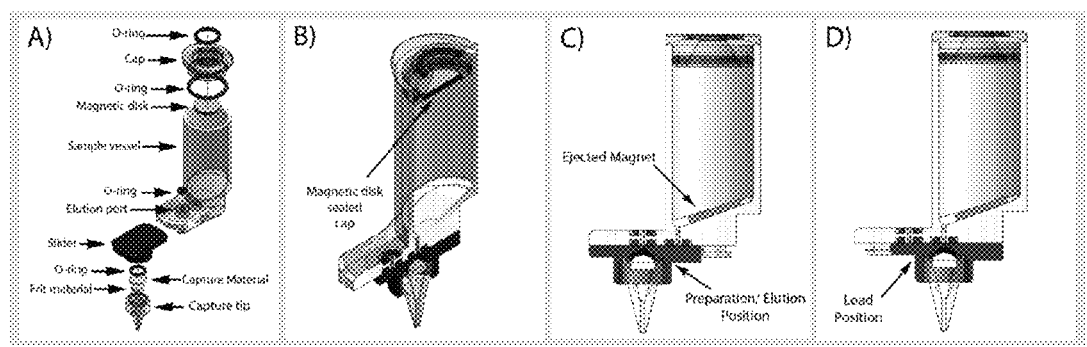
FIG. 33 depicts a non-limiting embodiment of a cartridge according to the claimed invention.

To enable completely automated sample preparation, a consumable was designed to allow all sample preparation steps to be conducted in a single cartridge (FIG. 33). In the field of molecular diagnostics, typically larger samples sizes, rather than smaller samples, are required to attain the necessary assay sensitivity. As a result the consumable module was designed to process samples as large as 1.0 ml of raw sample input.

In the exemplary embodiment shown in FIG. 33, samples are processed in a self-contained multi-component sample cartridge. The single use consumable is contains a tubular reaction chamber which is connected through a slide to a capture material that facilitates samples extraction. This slide allows the capture material to be positioned to either mix, capture or elute the purified sample. (A) shows an exploded view of the consumable. In (B), the cartridge is positioned to receive a sample, with the disk is secured in the sample cap to prevent leakage of the sample out of the cap of the consumable. In (C), the magnet is ejected from the sample cap to enable mixing of sample and reagents. In (D), the slider is located in the purge position, with the capture material positioned to be in fluid communication with the reaction chamber.

Figure 32:
FIG. 32 depicts a non-limiting embodiment of a system according to the claimed invention.

A non-limiting embodiment of a system according to the claimed invention is shown in FIG. 32. In this embodiment, the embodiment, is a bench top system that occupies approximately 12 cubic feet. The system suitably allows for front access for sample cartridge loading and removal. The system is suitably controlled through the use of a touch screen located on the upper right side of the instrument. Solutions are housed in the front case, which the exception of the removable waste container, which is located at the base of the instrument beneath the fluidic modules.

For some methods, typically using chaotropic salts and alcohol based precipitation methods, this requires a vessel that has a volume of approximately 10× of the original sample size. For these methods, the consumable cartridge was designed to contain a volume of approximately 10.0 ml of fluid volume. To enable lysis, preparation, and purification of robust organisms the ability to effectively mix the sample, with the variety of enzymes, buffers and solvents added to the sample is a design criterion.

As seen in an exploded view (FIG. 33A), the multiple component consumable is designed to achieve this functionality. To enable sample containment and mixing, use was made of a magnetic disk that serves two functions. First, the disk serves to seal the cartridge during sample loading and transport of the consumable to the instrument. This sample containment is critical when processing samples that contain potentially hazardous pathogenic agents. To accomplish this the disk was designed to be press fit inserted in to the cartridge cap to prevent liquid flow out of the top of the consumable during filing and transport to the instrument (FIG. 33A-B).

Once loaded on to instrument this disk is ejected from the sample cap (FIG. 33C) in order to enable its second function. Having been ejected from the sample cap the disk is now located within the sample fluid. Depending on the extraction method a series of buffers is injected into the consumable cartridge. During these filing steps, each magnet, controlled individually, can be rotated to enable non-contact mixing of the enzymes, buffer and alcohols within the consumable cartridge, which reduces or eliminates the possibility of sample to sample carryover cross contamination.

Extraction and purification of the target analytes is performed using a capture material located at the base of the consumable cartridge. This capture material is contained within a movable sliding component, termed the "slider" (FIG. 33A). The slider is connected to the consumable base on a rail system that enables the capture material to spatially located at one of two positions in the current embodiment of the consumable cartridge. In the first position that capture material is positioned directly under the elution port (FIG. 33C). The slider is located in this position while preparation steps prior to the capture step are conducted. At the conclusion of the temperature controlled enzymatic and buffer incubation steps this slider is actuated to move into a second position where target analyte extraction on the capture material is conducted (FIG. 33D).

During this extraction step the consumable module is suitably positioned directly beneath an air input line that, when contacted to the consumable, enables pressurization of the cartridge by the instrument. This pressurization forces the prepared sample through the capture material enabling analyte extraction. Once extracted, several washes of the internal vessel of the consumable cartridge are conducted by alternating the dispensing of solutions with the pressurization of the consumable. When these washes are completed the consumable is blown dry while being heated. This step is used to remove ethanol, which can inhibit enzymes used in downstream molecular diagnostic assays such as PCR and sequencing. When this capture material step is complete, the slider is again moved into the first position directly underneath the elution port on the consumable base (FIG. 33C) in order to remove the purified sample from the consumable device.

Sample Preparation in the cartridge is performed in coordination with the consumable module (FIG. 3). A useful feature of any sample preparation system or molecular diagnostic analysis platform is the ability to limit or eliminate sample cross contamination. This may be achieved by performing non-contact filing and mixing by designing a consumable module (FIG. 34) that is able to externally direct the internal workings of the cartridge.

Figure 34:
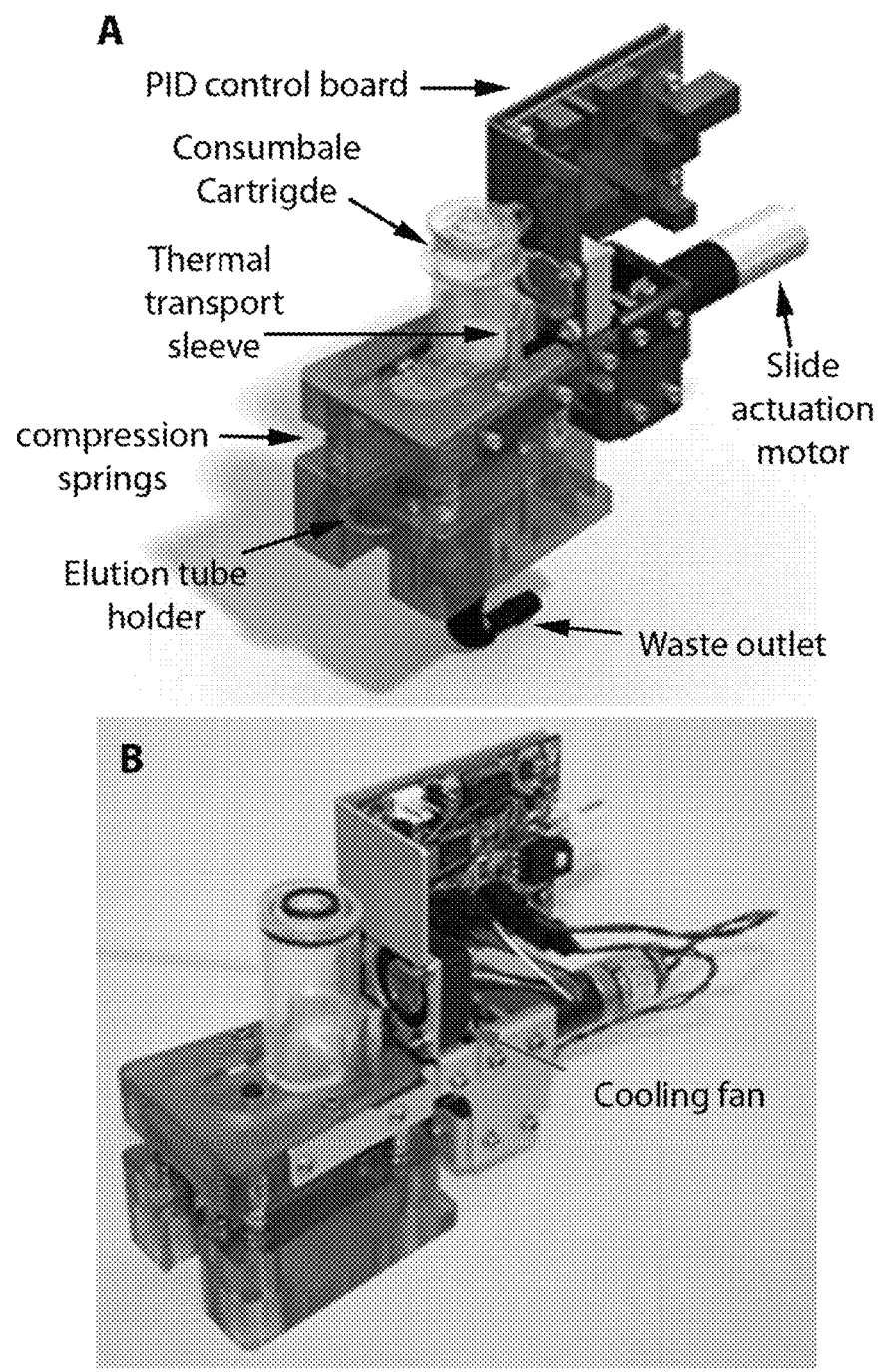
FIG. 34 depicts a non-limiting embodiment of a cartridge-receiving module according to the claimed invention.

In the non-embodiment of FIG. 34, consumables are used in conjunction with a module that performs elution tip positioning, non-contact mixing and thermocontrol of the cartridge. This module (A) may perform stand-alone sample preparation by having onboard PID control of the module functions, as well fluid connectivity to outgoing waste stream. The module is suitably spring loaded to enable reproducible compression of the consumable to the system fluid manifold. An alternate view is shown in FIG. 34B, which shows a cooling fan used to adjust the cartridge temperature.

Figure 35:
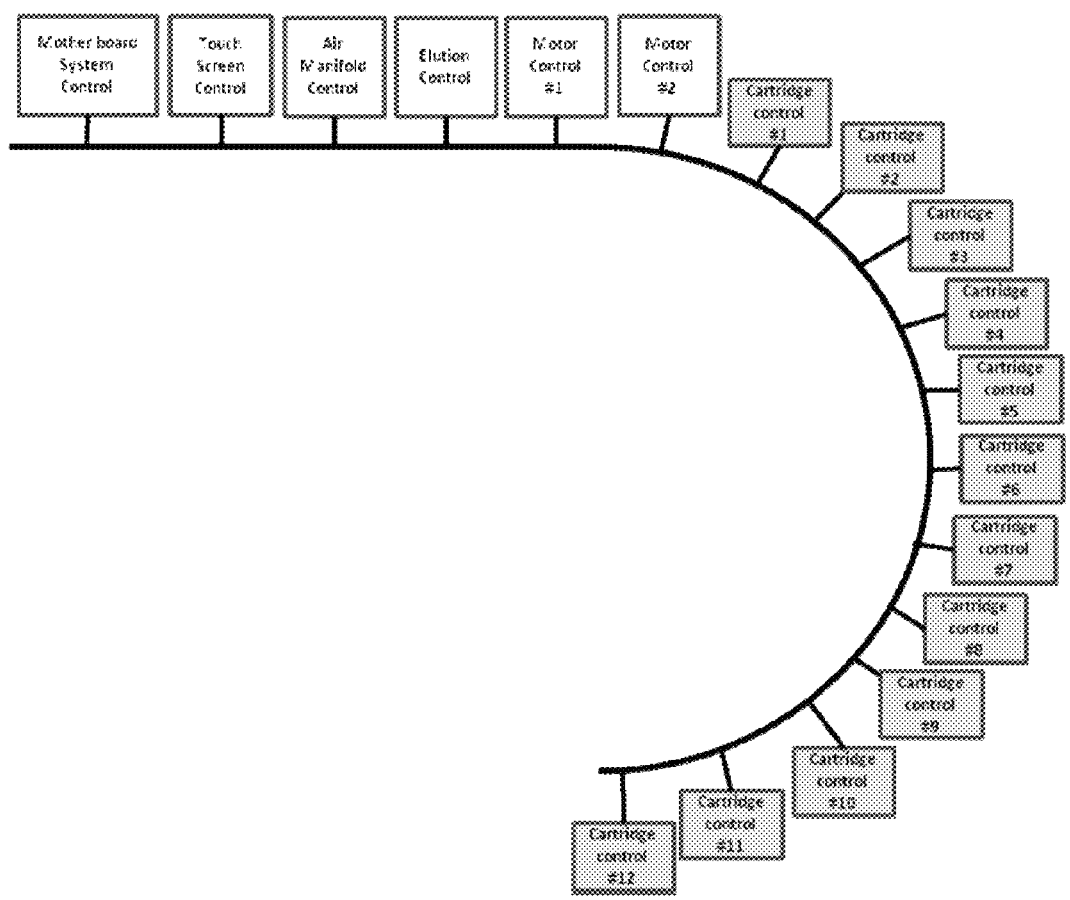
FIG. 35 depicts an exemplary CAN system layout of the claimed invention.

As a non-limiting example, the loading of buffer and solvents is performed using a nozzle that positioned to allow the solutions to be added to the consumable cartridge without contacting the sample itself. To enable rotation of the magnetic disk, a rare earth magnet is located at the base of the cartridge approximately 2 cm from the base of the consumable cartridge. This magnet is be rotated on axis at variable speeds for a duration that is scripted to the individual consumable module. The individual modules are operated independently using, for example, a Controller Area Network (CAN) communication system (FIG. 35). CAN is a message based protocol, useful for industrial automation and medical equipment. This system enables each consumable module to operate an individual script during a single sample preparation run.

Each consumable module may contain a discrete electronics hardware and software package that are slaved to the central controller. This electronic package enables the central controller or motherboard to execute high level commands communicated to the slaved consumable module that can operate PID control of the temperature, mixing and slider motion control. In this way the mother board contains all of the high level commends for the various methods that can be operated in tandem.

The instrument is suitably constructed to create a partition between the major electrical components and fluidic components. In some embodiments, the system compartmentalizes the pumps, mother board, and touch screen on the right side of the instrument, while the consumable modules, waste and elution manifolds are located on the left compartment of the instrument—this separates these components in the event of a failure to contain any system fluids.

In one non-limiting embodiment, the system accommodates twelve consumable modules on a rotary platen. In this format the consumable cartridges can be positioned at various dispensing and air flow ports to enable automated preparation of any number of samples up to the full complement of consumable modules.

As described each module has the ability to operate independently of one another to enable random access sample preparation. These modules are linked into the motherboard using a standard 14 pin connector to allow communication of the high level commands to each module. The modules are also suitably connected to a waste manifold at the base of the instrument. This manifold evacuates waste from the capture tip under vacuum, without actually contacting the capture tip, which prevents contaminants such as chaotropic buffers and alcohol accumulating on the external surface of the capture tip. If these contaminants are not removed they can inhibit the downstream molecular diagnostic analysis.

During the extraction of the samples this capture interfaces with this manifold to remove the chaotropic buffers and alcohols to a waste container located at the base of instruments. This waste container is suitably connected to the waste manifold using a quick connect system that enable to user to remove the waste drawer disconnect the line and dump the accumulated liquids.

The system which consists of the consumable cartridge, the consumable module, along with the system software and hardware works in concert to completely automate the sample preparation procedure. The process of sample preparation is essentially a series of commands, that when used with a particular set of reagents, produces purified samples for downstream molecular diagnostic assays. Useful parameters include 1) temperature control, 2) sample and reagent mixing and 3) sample elution.

Figure 36:
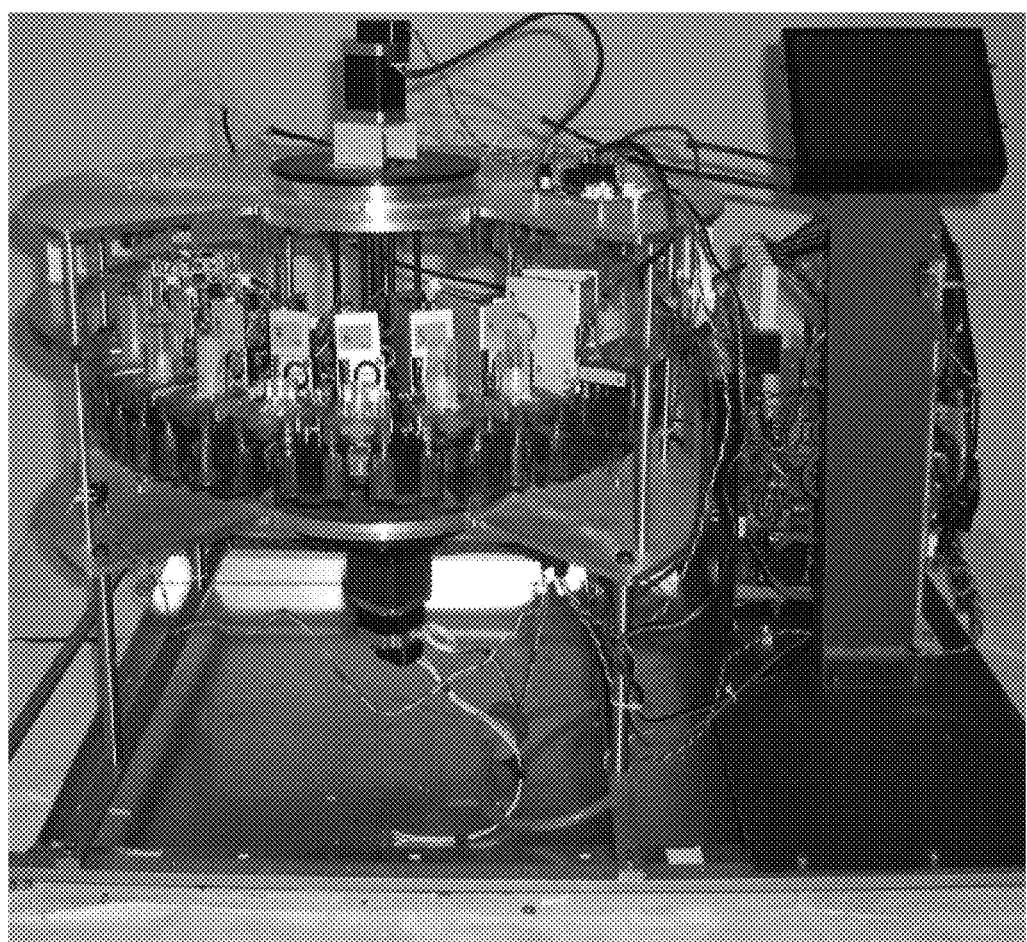
FIG. 36 depicts a non-limiting embodiment of the claimed invention.

To perform this sample preparation process the user places the consumable in a processing system 200 that includes a rack that is designed to contain several cartridges 101, such as shown by non-limiting FIG. 36. The samples may be loaded within a biosafety cabinet. Once loaded the consumable cartridges are transported to the instrument for loading on the consumable module within the instrument. The user first actuates the touch screen and selects the intended method desired. The consumable device is then presented to a bar code scanner which verifies the method selected and the loading position. The touch screen then indicates the system is ready for loading. The User then opens the front access door, and inserts the consumable cartridge in to the consumable module which is a "snap" fit. In a similar fashion each consumable is loaded, and when complete, the user again uses the touch screen to start the preparation run.

To elute the sample the consumable cartridge is located beneath a manifold that is designed to dispense both air and fluid through this O-ring seated orifice. Once contacted, the capture material is blown dry under temperature control. Once dry an elution buffer is loaded onto capture material to enable removed of the purified analytes.

Once the preparation run in actuated, the system suitably ejects the magnetic disks from the sample cap into the fluid sample (FIG. 33). The appropriate buffers are then added to the consumable and the samples are mixed using the magnetic disk apparatus. Depending on the application that is employed on the system, several incubations at a various temperatures are required.

In some embodiments, temperature control is accomplished by a resistive heater that conducts heat to the consumable cartridge through an aluminum block that encases the consumable. Temperature control is effected by PID controls in combination with a thermocouple that monitors an aluminum heat transfer block. In a representative example, four modules were heated while measuring both the external block temperature as well as the internal fluid temperature. In one embodiment, the first temperature step (typically used for the lysozyme incubations) was could reached in approximately 2 min, by heating the external block to 65 deg. C. No significant variation in the internal fluid temperature was found over a period of approximately 15 minutes. A second incubation may be used when whole blood samples are being processed. This second incubation makes use of proteinase K, a proteolytic enzyme the digests the protein content of the sample. To reach 56 deg. C., the heating block temperature was increased to approximately 100 deg. C. for a period of approximately 3 minutes; the internal fluid temperature increased rapidly to 56 deg. C., and was stable over a period of 15 minutes, the required time for effective protein digestion.

The final step in several applications is the denaturing of the nucleic acid. To reach the required temperature the aluminum block was heated to approximately 120° C. for a period of 1 minute then lowered to 110° C. for a period of 10 minutes. While temperature ramp was slower the samples did reach the required temperature for effective nucleic acid denaturation, 95 deg. C., and again was stable for a period of approximately 15 minutes. At the conclusion of this denaturation step a fan located on the back of the aluminum block was activated. This fan cools the aluminum block by convection, and was able to rapidly cool the heating block back to room temperature in approximately 1 minute. Cooling of the internal fluids was also reduced to room temperature.

With the incubation steps complete the next phase of the sample preparation is conducted. For several of the applications used on this system the samples require the addition of a chaotropic buffer and the addition of alcohols to facilitate the precipitation of the liberated nucleic acids. To achieve effective mixing of the digested samples, a magnetic disk (FIG. 33) was used, that when rotated created a vortex effect in the sample preparation chamber.

The rotational axis of the disk was one factor in the ability to perform effective mixing which would result in high efficiency nucleic acid extraction. To evaluate the extraction of nucleic acids, samples extraction of 1.0 ml blood samples that contained Epstein Barr Viral (EBV) DNA was performed.

Increased mixing speed, resulted in increased yields of nucleic acid; by increasing the duration of the mixing step, it was found that EBV DNA extraction yields were equivalent to bench top protocols for extraction of large volume (1.0 ml) blood samples.

When the mixing steps were complete, in a concerted series of actuations as described above (FIGS. 33-36), the sample is pushed through the consumable to allow for capture of the nucleic acids on a material that extracts the sample analytes from the mixture of enzymes, buffers and solvents. With the sample prepared for extraction the slider component is positioned by the system into the "load" position. Each consumable cartridge is then positioned beneath the "purge" port. The system raises the consumable module platen to compress the springs within the consumable modules and form an air tight seal between the air port and the sample cap of the cartridge. With the seal pressure tight, the consumable is pressurized to force the prepared sample through the capture material as described above. Sensors with the system architecture monitor the purge pressure during this operation. At the point where these sensors detect a significant pressure drop a valve is actuated to stop the pressurization of the consumable. In addition this system suitably includes a time out feature that will notify the user if a sample will not flow through the capture material, an important feature to preserve precious samples if there are not properly loaded.

Once loaded, wash buffers are suitably dispensed into the consumable cartridge to remove unwanted contaminants remaining within the consumable cartridge and on the capture material. The number of washes may vary depending on the turbidity and protein load of the sample being prepared.

The final step in the purification process is suitably removal of the remaining fluids contained within the capture material. Air is suitably conducted through the capture material to remove any additional contaminants prior to the final elution step.

Upon sample loading and purification, the system prepares for the elution of the sample. In this step the consumables are suitably rotated upon the paten to the elution manifold. Once positioned beneath the elution manifold that slider (FIG. 33) is positioned the capture material orifice beneath the elution port on the consumable base. With the consumable in the elution position, the system then compresses the consumable module against the elution manifold to form a pressure tight seal between the elution port of the consumable and the ports located on the elution manifold. The system then dispenses the elution buffer through the capture tip to elute the sample, e.g., not a micro centrifuge tube located beneath the capture tip.

In one sample exemplary embodiment, reproducible elution volumes were achievable. When a volume of 200 ul was delivered to a consumable cartridge at each position the automated system, an approximate dead volume of 20 ul was found, as judged by the delivery of approximately 180 ul to each position. Over 100 runs, the elution volume had an approximate 6.0% average coefficient of variation.

Non-limiting embodiments were tested on viral DNA, from Epstein Barr virus, total rat RNA, and finally bacterial DNA from *E. coli*. Extraction efficiencies were determined by real time PCR using a Roche LC 480 real time PCR analysis system, as described elsewhere herein.

The consumable module suitably includes three main functionalities that are PID controlled by the module electronic board. The first of these functions is the magnetic mixing, which mixing is suitably effected using a motor driven rotational motion that when actuated forces rotation of the magnetic disk within the fluid containing vessel.

A second operation of the consumable module is the temperature control of the consumable. Fully automated sample preparation may include the use of multiple enzymes that have optimally proteolytic or nucleolytic activity at temperatures above 25 deg. C.

To perform the incubation with the consumable cartridge, an aluminum sleeve may be used to transfer and extract heat from the consumable module. This sleeve is suitably heated using a thermoelectric cooler under PID control to raise and maintain the internal temperature of the consumable cartridge (FIG. 34).

Another consideration is the ability to remove heat from the consumable. After the heated incubations are complete, a fan located on the back of the thermoelectric cooler is activated which, by convection, removes heat from the consumable module and the consumable cartridge.

One method is applied to gram positive bacterial extraction in whole blood. This protocol currently uses three incubation steps for the preparation of the sample for extraction.

The first incubation may use a lysozyme and use an incubation at about 37 deg. C. for a period of 5-45 minutes depending on the bacterial species. A second incubation may use a proteinase K step, which is useful in allowing extraction of sample analytes from whole blood. A suitable incubation temperature for this step is about 56 deg. C., with a duration of at least about 15 minutes.

An additional incubation is useful to denature the genomic DNA at 95 deg. C. to increase the efficiency of the extraction.

With heaters under PID control, a control script is suitably used to control the external temperature of the cartridge and the internal temperature of the cartridge. Sample were cooled to room temperature within about 3-5 minutes after the 95 deg. C. step.

A further operation includes positioning of the capture tip between the elution port and the sample capture port. This positioning of this tip is suitably controlled by a gear driven DC motor that actuates an aluminum plate that resides beneath the consumable cartridge.

At various times during the sample preparation procedure this gear driven plate is suitably actuated between the capture and elution positions. In this way the sample preparation, alcohols, and wash buffer components, are physically separated from the elution tip.

What is claimed is:

1. A processing system configured to concentrate and isolate cellular components, comprising:
    a plurality of cartridge receivers, each cartridge receiver having a recess configured to receive a purification cartridge, the purification cartridge including a sample vessel, an elution port, and a capture chamber, the capture chamber being slidably affixed relative to the sample vessel and elution port, the capture chamber defining a void in which a capture material is disposed;
    a motor configured to actuate the capture chamber from a load position, in which the capture material is in fluid communication with the sample vessel, to an elution position, in which the capture material is in fluid communication with an elution port;
    a controller configured to control the motor; and
    a tube extending from the cartridge receiver that, when the capture chamber is in the load position, is in fluid communication with the sample vessel and capture material.

2. The system of claim 1, wherein the controller is capable of modulating processing of two different samples.

3. The system of claim 2, wherein the controller is capable of modulating simultaneous processing of two or more different samples.

4. The system of claim 2, wherein the controller is capable of modulating sequential processing of two or more different samples.

5. The processing system of claim 1, further comprising a thermal element configured to contact at least a portion of the purification cartridge.

6. The processing system of claim 5, further comprising a shield disposed about the thermal element.

7. The processing system of 1 further comprising at least one magnet configured to secure the purification cartridge in one of the plurality of cartridge receivers.

8. The processing system of 1 further comprising at least one spring loaded grip configured to secure the purification cartridge in one of the plurality of cartridge receivers.

9. The processing system of 1 wherein the controller is further configured to control the system so as to process two different samples at one time.

10. A processing system, comprising:
    a plurality of purification cartridges, each cartridge including a sample vessel, an elution port, and a capture chamber, the capture chamber being slidably affixed relative to the sample vessel and elution port, the capture chamber defining a void in which a capture material is disposed;
    a plurality of cartridge receivers, each receiver defining a slot in which one of the plurality of purification cartridges is disposed;
    a motor configured to actuate the capture chamber from a load position, in which the capture material is in fluid communication with the sample vessel, to an elution position, in which the capture material is in fluid communication with an elution port;
    a controller configured to control the motor; and
    a tube extending from the cartridge receiver that, when the capture chamber is in the load position, is in fluid communication with the sample vessel and capture material.

11. The fluid processing system of claim 10, wherein the controller is capable of effecting different processing steps for two or more of two or more samples disposed in two or more purification cartridges disposed in two or more cartridge receivers.

12. The processing system of claim 10 wherein the controller is further configured to control the system so as to effect processing of two or more different samples disposed in two or more purification cartridges disposed in two or more cartridge receivers.

13. The processing system of claim 10, further comprising at least one thermal element configured to contact at least a portion of at least one of the plurality of purification cartridges.

14. The processing system of 10 further comprising at least one magnet configured to secure at least one of the plurality of purification cartridges in one of the plurality of cartridge receivers.

15. The processing system of 10 further comprising at least one spring loaded grip configured to secure at least one of the plurality of purification cartridges in one of the plurality of cartridge receivers.

16. The processing system of 10 wherein the capture material includes at least one of a microarrays, a porous polymer monolith, a silica membrane, a cellulose packing material, a polycarbonate membranes, and a sequencing flow cell.

17. The processing system of claim 10, wherein the purification cartridge includes a magnet configured to mix a sample in the sample vessel.

18. A processing system, comprising:
   a plurality of cartridge receivers, each receiver having a recess configured to hold at least part of a purification cartridge, the purification cartridge including a sample vessel, an elution port, and a capture chamber, the capture chamber being slidably affixed relative to the sample vessel and elution port, the capture chamber defining a void in which a capture material is disposed;
   at least one of the plurality of cartridge receivers including a thermal element configured to heat a molecular capture region on the purification cartridge to above about 40° C., or to cool the molecular capture region to below about 10° C., or both; and
   a motor configured to actuate the capture chamber from a load position, in which the capture material is in fluid communication with the sample vessel, to an elution position, in which the capture material is in fluid communication with an elution port; and
   a controller configured to control the motor.

19. The processing system of claim 18, further comprising a shield disposed about the thermal element.

20. The processing system of 18 further comprising at least one magnet configured to secure the purification cartridge in one of the plurality of cartridge receivers.

21. The processing system of 18 further comprising at least one spring loaded grip configured to secure the purification cartridge in one of the plurality of cartridge receivers.

22. The processing system of 18 wherein the controller is further configured to control the system so as to process two different samples at one time.

* * * * *